US011898207B2

(12) United States Patent
Lu et al.

(10) Patent No.: US 11,898,207 B2
(45) Date of Patent: Feb. 13, 2024

(54) METHODS OF ISOLATING NEOANTIGEN-SPECIFIC T CELL RECEPTOR SEQUENCES

(71) Applicant: The United States of America, as represented by the Secretary, Department of Health and Human Services, Bethesda, MD (US)

(72) Inventors: Yong-Chen Lu, Rockville, MD (US); Peter Fitzgerald, Silver Spring, MD (US); Zhili Zheng, Gaithersburg, MD (US); Steven A. Rosenberg, Potomac, MD (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 999 days.

(21) Appl. No.: 16/495,508

(22) PCT Filed: Mar. 28, 2018

(86) PCT No.: PCT/US2018/024828
§ 371 (c)(1),
(2) Date: Sep. 19, 2019

(87) PCT Pub. No.: WO2018/183485
PCT Pub. Date: Oct. 4, 2018

(65) Prior Publication Data
US 2020/0056237 A1 Feb. 20, 2020

Related U.S. Application Data

(60) Provisional application No. 62/479,398, filed on Mar. 31, 2017.

(51) Int. Cl.
| | | |
|---|---|---|
| A61K 35/17 | (2015.01) | |
| C12Q 1/6881 | (2018.01) | |
| G16B 30/10 | (2019.01) | |
| G16B 30/20 | (2019.01) | |
| C07K 14/725 | (2006.01) | |
| C12N 5/0783 | (2010.01) | |
| C12N 15/10 | (2006.01) | |

(52) U.S. Cl.
CPC ............ C12Q 1/6881 (2013.01); A61K 35/17 (2013.01); C07K 14/7051 (2013.01); C12N 5/0636 (2013.01); C12N 15/1003 (2013.01); C12N 15/1096 (2013.01); G16B 30/10 (2019.02); G16B 30/20 (2019.02); *C12N 2502/30* (2013.01)

(58) Field of Classification Search
CPC .................................................... A61K 35/17
See application file for complete search history.

(56) References Cited

U.S. PATENT DOCUMENTS

| | | |
|---|---|---|
| 8,034,334 B2 | 10/2011 | Dudley et al. |
| 8,383,099 B2 | 2/2013 | Dudley et al. |
| 2012/0244133 A1 | 9/2012 | Rosenberg et al. |
| 2015/0337369 A1 | 11/2015 | Davis et al. |

FOREIGN PATENT DOCUMENTS

| | | | |
|---|---|---|---|
| EP | 2 367 000 A1 | 9/2011 | |
| WO | WO 2016/053338 A1 | 4/2016 | |
| WO | WO 2016/053339 A1 | 4/2016 | |
| WO | WO 2016/179006 A1 | 11/2016 | |
| WO | WO 2017/048593 A1 | 3/2017 | |
| WO | WO-2017048614 A1 * | 3/2017 | ......... A61K 39/0011 |

OTHER PUBLICATIONS

Zha et al. (Oncotarget. Dec. 20, 2016; 7 (51): 84246-57).*
Wang et al., "T cell receptor αβ diversity inversely correlates with pathogen-specific antibody levels in human cytomegalovirus infection" and Supplementary Materials, *Sci. Transl. Med.*, 4(128): 128ra42 (2012).
Cohen et al., "Enhanced antitumor activity of murine-human hybrid T-cell receptor (TCR) in human lymphocytes is associated with improved pairing and TCR/CD3 stability," *Cancer Res.*, 66: 8878-8886 (2006).
Cohen et al., "Enhanced antitumor activity of T cells engineered to express T-cell receptors with a second disulfide bond," *Cancer Res.*, 67: 3898-3903 (2007)
Dudley et al., "Generation of tumor-infiltrating lymphocyte cultures for use in adoptive transfer therapy for melanoma patients," *J. Immunother.*, 26(4): 332-342 (2003).
Haga-Friedman et al., "Incorporation of transmembrane hydrophobic mutations in the TCR enhance its surface expression and T cell functional avidity," *J. Immunol.*, 188(11): 5538-5546 (2012).
Guo et al., "Rapid cloning, expression, and functional characterization of paired αβ and γδ T-cell receptor chains from single-cell analysis," *Mol. Ther.*, 3: 15054 (2016).
Han et al., "Linking T-cell receptor sequence to functional phenotype at the single-cell level," *Nature Biotechnol.*, 32: 684-692 (2014).
International Bureau, International Search Report and Written Opinion in International Application No. PCT/US2018/024828, dated Jun. 29, 2018.

(Continued)

*Primary Examiner* — Stephen L Rawlings
(74) *Attorney, Agent, or Firm* — Leydig, Voit & Mayer

(57) ABSTRACT

Disclosed are methods of isolating paired T cell receptor (TCR) alpha and beta chain sequences, or an antigen-binding portion thereof. Also disclosed are methods of automatically identifying the TCR alpha and beta chain V segment sequences and CDR3 sequences of a TCR having antigenic specificity for a mutated amino acid sequence encoded by a cancer-specific mutation. Methods of preparing a population of cells that express paired TCR alpha and beta chain sequences, or an antigen-binding portion thereof, are also disclosed. Isolated pairs of TCR alpha and beta chain sequences and isolated populations of cells prepared by the methods are also disclosed.

10 Claims, 17 Drawing Sheets

Specification includes a Sequence Listing.

(56) References Cited

OTHER PUBLICATIONS

Kobayashi et al., "A new cloning and expression system yields and validates TCRs from blood lymphocytes of patients with cancer within 10 days," *Nature Med.*, 19: 1542-1546 (2013).

Lefranc et al., "IMGT®, the international ImMunoGeneTics information system® 25 years on," *Nucleic Acids Res.*, 43: D413-422 (2015).

Lefranc et al., "Using Bioinformatics Tools for the Sequence Analysis of Immunoglobulins and T Cell Receptors," *Current Protocols in Immunol.*, A.1W.1-A.1W.15 (2006).

Li et al., "Fast and accurate short read alignment with Burrows-Wheeler transform," *Bioinformatics*, 25(14): 1754-1760 (2009).

Li et al., "Fast and accurate long-read alignment with Burrows-Wheeler transform," *Bioinformatics*, 26(5): 589-595 (2010).

Linnemann et al., "High-throughput identification of antigen-specific TCRs by TCR gene capture," *Nature Med.*, 19: 1534-1541 (2013).

Lu et al., "An efficient Single-Cell RNA-Seq Approach to Identify Neoantigen-Specific T Cell Receptors," *Mol. Ther.*, 26(2): 379-389 (2018).

Lu et al., "Efficient identification of mutated cancer antigens recognized by T cells associated with durable tumor regressions," *Clin. Cancer Res.*, 20(13): 3401-3410 (2014).

Morgan et al., "Cancer regression in patients after transfer of genetically engineered lymphocytes," *Science*, 314: 126-129 (2006).

Riddell et al., "The use of anti-CD3 and anti-CD28 monoclonal antibodies to clone and expand human antigen-specific T cells," *J. Immunol. Methods*, 128: 189-201 (1990).

Ronaghi et al., "A sequencing method based on real-time pyrophosphate," *Science*, 281(5375): 363-365 (1998).

Stubbington et al., "T cell fate and clonality inference from single cell transcriptomes," *Nature Methods*, 13(4): 329-332 (2016).

Tran et al., "Cancer Immunotherapy Based on Mutation-Specific CD4+ T Cells in a Patient with Epithelial Cancer," *Science*, 344: 641-645 (2014).

Tran et al., "Immunogenicity of somatic mutations in human gastrointestinal cancers," *Science*, 350: 1387-1390 (2015).

Voelkerding et al., "Next-generation sequencing: from basic research to diagnostics," *Clinical Chemistry*, 55(4): 641-658 (2009).

Wargo et al., "Recognition of NY-ESO-1+ tumor cells by engineered lymphocytes is enhanced by improved vector design and epigenetic modulation of tumor antigen expression," *Cancer Immunol. Immunother.*, 58: 383-394 (2009).

Zhang et al., "The impact of next-generation sequencing on genomics," *J. Genet. Genomics*, 38(3): 95-109 (2011).

Parkhurst et al., "Isolation of T-Cell Receptors Specifically Reactive with Mutated Tumor-Associated Antigens from Tumor-Infiltrating Lymphocytes Based on CD137 Expression", *Clinical Cancer Research*, vol. 23, Issue 10, pp. 2491-2505 (2017).

\* cited by examiner

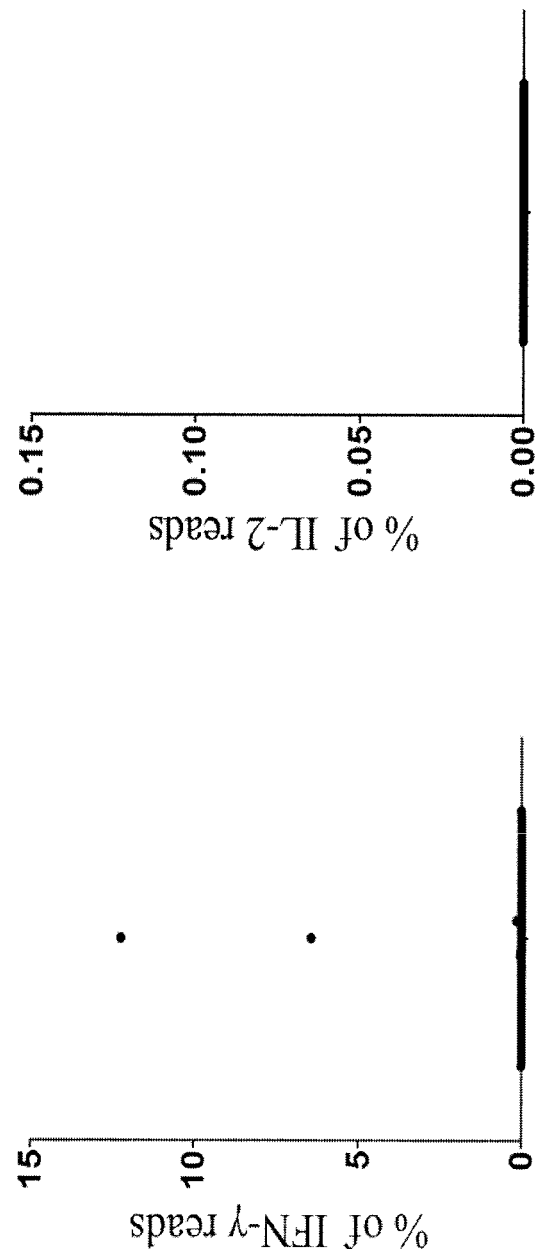

```
                                    400
                                         ↘

┌─────────────────────────────────────────────────────────────────────────┐
│   Receive sequences of the multiple fragments of cDNA of a single identified T cell │
│                                    402                                   │
└─────────────────────────────────────────────────────────────────────────┘
                                    ↓
┌─────────────────────────────────────────────────────────────────────────┐
│ Aligning the sequences of each of the multiple fragments of cDNA to a reference TCR │
│ sequence database to identify TCR alpha chain variable (V) segment sequences and    │
│ TCR beta chain V segment sequences of the multiple fragments of cDNA of the single  │
│                         T cell identified 403                           │
└─────────────────────────────────────────────────────────────────────────┘
                                    ↓
┌─────────────────────────────────────────────────────────────────────────┐
│   identifying TCR CDR3 sequences in the multiple fragments of cDNA containing the   │
│   TCR alpha chain V segment sequences identified and in the multiple fragments of   │
│       cDNA containing the TCR beta chain V segment sequences identified             │
│                                    404                                              │
└─────────────────────────────────────────────────────────────────────────┘
                                    ↓
┌─────────────────────────────────────────────────────────────────────────┐
│   counting the number of multiple fragments of cDNA which share the same alpha chain│
│      CDR3 amino acid sequence and the number of multiple fragments of cDNA which    │
│              share the same beta chain CDR3 amino acid sequence                     │
│                                    405                                              │
└─────────────────────────────────────────────────────────────────────────┘
                                    ↓
┌─────────────────────────────────────────────────────────────────────────┐
│ collecting the highest number of multiple fragments of cDNA which encode the same   │
│ alpha chain CDR3 sequence, the highest number of multiple fragments of cDNA which   │
│ encode the same beta chain CDR3 sequence and, optionally, the second highest        │
│ number of multiple fragments of cDNA which encode the same alpha chain CDR3         │
│ sequence 406                                                                        │
└─────────────────────────────────────────────────────────────────────────┘
                                    ↓
┌─────────────────────────────────────────────────────────────────────────┐
│ identifying the TCR alpha chain V segment sequence of the highest number of multiple│
│ fragments of cDNA collected, the TCR beta chain V segment sequence of the highest   │
│ number of multiple fragments of cDNA collected and, optionally, the TCR alpha chain V│
│ segment sequence of the second highest number of multiple fragments of cDNA         │
│ collected to identify the TCR alpha and beta chain V segment sequences 407          │
└─────────────────────────────────────────────────────────────────────────┘
```

FIG. 8

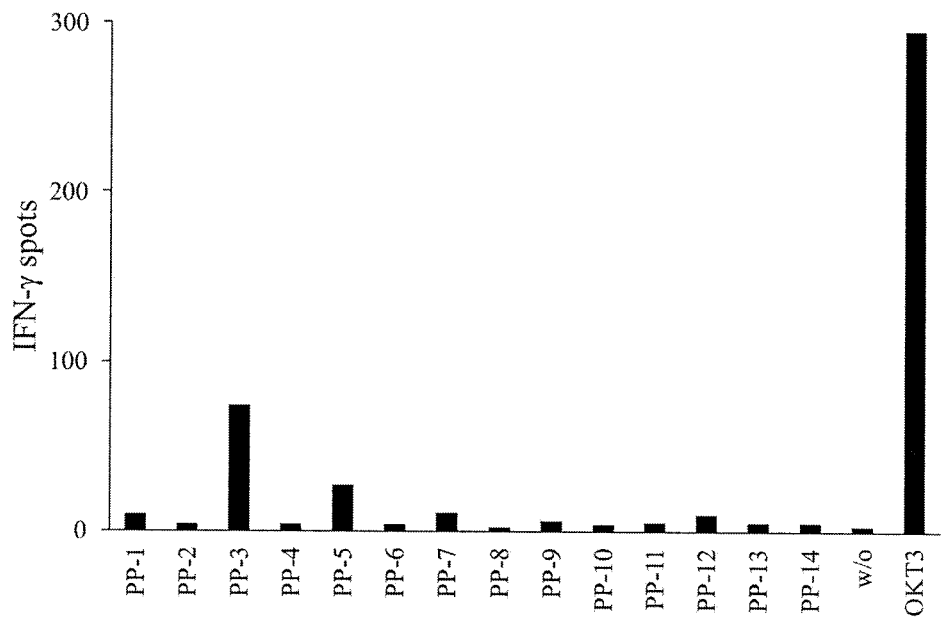
FIG. 9A
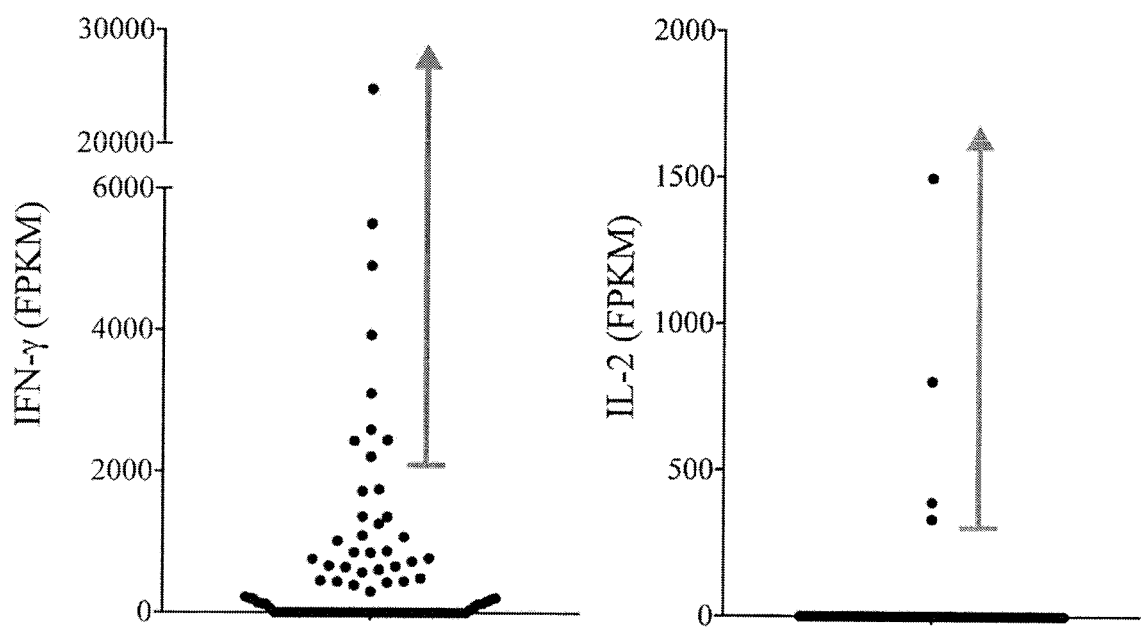
FIG. 9B
FIG. 9C

METHODS OF ISOLATING NEOANTIGEN-SPECIFIC T CELL RECEPTOR SEQUENCES

CROSS-REFERENCE TO RELATED APPLICATIONS

This patent application is the U.S. national stage of PCT/US2018/024828, filed Mar. 28, 2018, which claims the benefit of U.S. Provisional Patent Application No. 62/479,398, filed Mar. 31, 2017, each of which is incorporated by reference in its entirety herein.

STATEMENT REGARDING FEDERALLY SPONSORED RESEARCH AND DEVELOPMENT

This invention was made with Government support under project number ZIABC010985 awarded by the National Institutes of Health, National Cancer Institute. The Government has certain rights in this invention.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 5,577 Byte ASCII (Text) file named "744531_ST25.txt" dated Sep. 18, 2019.

BACKGROUND OF THE INVENTION

Adoptive cell therapy (ACT) using cells that have been genetically engineered to express a cancer antigen (e.g., neoantigen)-specific T cell receptor (TCR) can produce positive clinical responses in some cancer patients. Nevertheless, obstacles to the successful use of TCR-engineered cells for the widespread treatment of cancer and other diseases remain. For example, TCRs that specifically recognize cancer antigens (e.g., neoantigens) may be difficult to identify and/or isolate from a patient. Accordingly, there is a need for improved methods of obtaining cancer-reactive (e.g., neoantigen-reactive) TCRs.

BRIEF SUMMARY OF THE INVENTION

An embodiment of the invention provides a method of isolating paired T cell receptor (TCR) alpha and beta chain sequences, or an antigen-binding portion thereof, the method comprising: (a) isolating, from a biological sample, T cells having antigenic specificity for a mutated amino acid sequence encoded by a cancer-specific mutation; (b) co-culturing the isolated T cells with antigen presenting cells (APCs) that present the mutated amino acid sequence so that the T cells express one or more T cell activation markers; (c) sorting the co-cultured T cells into separate single T cell samples; (d) isolating mRNA from each separate single T cell sample; (e) sequencing the mRNA from each separate single T cell sample, wherein the sequencing comprises: (i) producing cDNA from the mRNA and amplifying the cDNA; (ii) producing multiple fragments of the amplified cDNA and tagging the multiple fragments; (iii) amplifying the tagged, multiple fragments of the cDNA; and (iv) sequencing the amplified, tagged multiple fragments of the cDNA; wherein the sequencing identifies the sequences of each of the multiple fragments of cDNA; (f) aligning the sequences of each of the multiple fragments of cDNA to a known sequence of the one or more T cell activation markers to identify which single T cell sample contained a single T cell which expressed the one or more T cell activation markers; (g) aligning the sequences of each of the multiple fragments of cDNA to a reference TCR sequence database to identify TCR alpha chain variable (V) segment sequences and TCR beta chain V segment sequences of the multiple fragments of cDNA of each separate single T cell sample which was identified in (f) to express one or more T cell activation markers; (h) identifying TCR complementarity determining region 3 (CDR3) sequences in the multiple fragments of cDNA containing the TCR alpha chain V segment sequences identified in (g) and in the multiple fragments of cDNA containing the TCR beta chain V segment sequences identified in (g); (i) counting the number of multiple fragments of cDNA which share the same alpha chain CDR3 amino acid sequence and the number of multiple fragments of cDNA which share the same beta chain CDR3 amino acid sequence; (j) collecting the highest number of multiple fragments of cDNA which encode the same alpha chain CDR3 sequence, the highest number of multiple fragments of cDNA which encode the same beta chain CDR3 sequence and, optionally, the second highest number of multiple fragments of cDNA which encode the same alpha chain CDR3 sequence, wherein the alpha chain CDR3 sequence encoded by the second highest number of multiple fragments of cDNA is different from the alpha chain CDR3 sequence encoded by the highest number of multiple fragments of cDNA, to identify the TCR alpha and beta chain CDR3 sequences; (k) identifying the TCR alpha chain V segment sequence of the highest number of multiple fragments of cDNA collected in (j), the TCR beta chain V segment sequence of the highest number of multiple fragments of cDNA collected in (j) and, optionally, the TCR alpha chain V segment sequence of the second highest number of multiple fragments of cDNA collected in (j) to identify the TCR alpha and beta chain V segment sequences; and (l) assembling one or more nucleotide sequences encoding: a TCR alpha chain comprising the TCR alpha chain V segment sequence identified in (k) and the TCR alpha chain CDR3 sequence collected in (j) and a TCR beta chain comprising the TCR beta chain V segment sequence identified in (k) and the TCR beta chain CDR3 sequence collected in (j), optionally assembling a second one or more nucleotide sequences encoding: a second TCR alpha chain comprising the TCR alpha chain V segment sequence of the second highest number of multiple fragments of cDNA identified in (k) and the TCR alpha chain CDR3 sequence of the second highest number of multiple fragments of cDNA collected in (j) and the TCR beta chain comprising the TCR beta chain V segment sequence identified in (k) and the TCR beta chain CDR3 sequence collected in (j) to produce isolated paired TCR alpha and beta chain sequences, or an antigen-binding portion thereof.

Another embodiment of the invention provides a method of automatically identifying the T cell receptor (TCR) alpha and beta chain V segment sequences and CDR3 sequences of a TCR having antigenic specificity for a mutated amino acid sequence encoded by a cancer-specific mutation, the method comprising: (a) receiving, at a user computing device, sequences of multiple fragments of cDNA, wherein the cDNA is encoded by mRNA produced by a single T cell following co-culture of the T cell with antigen presenting cells (APCs) that present the mutated amino acid sequence so that the T cell expresses one or more T cell activation markers; (b) performing computerized alignment of the sequences of each of the multiple fragments of cDNA to a reference TCR sequence database to identify TCR alpha chain variable (V) segment sequences and TCR beta chain V segment sequences of the multiple fragments of cDNA; (c) performing computerized identification of TCR complementarity determining region 3 (CDR3) sequences in the multiple fragments of cDNA containing the TCR alpha chain V segment sequences identified in (b) and in the multiple fragments of cDNA containing the TCR beta chain V segment sequences identified in (b); (d) performing computerized counting of the number of multiple fragments of cDNA which share the same alpha chain CDR3 amino acid sequence and the number of multiple fragments of cDNA which share the same beta chain CDR3 amino acid sequence; (e) performing computerized collecting of the highest number of multiple fragments of cDNA which encode the same alpha chain CDR3 sequence, the highest number of multiple fragments of cDNA which encode the same beta chain CDR3 sequence and, optionally, the second highest number of multiple fragments of cDNA which encode the same alpha chain CDR3 sequence, wherein the alpha chain CDR3 sequence encoded by the second highest number of multiple fragments of cDNA is different from the alpha chain CDR3 sequence encoded by the highest number of multiple fragments of cDNA to identify the TCR alpha and beta chain CDR3 sequences; and (f) performing computerized identification of the TCR alpha chain V segment sequence of the highest number of multiple fragments of cDNA collected in (e), the TCR beta chain V segment sequence of the highest number of multiple fragments of cDNA collected in (e) and, optionally, the TCR alpha chain V segment sequence of the second highest number of multiple fragments of cDNA collected in (e) to identify the TCR alpha and beta chain V segment sequences.

Another embodiment of the invention provides a method of preparing a population of cells that express paired TCR alpha and beta chain sequences, or an antigen-binding portion thereof, the method comprising: isolating paired TCR alpha and beta chain sequences, or an antigen-binding portion thereof, according to any of the inventive methods described herein, and introducing a nucleotide sequence encoding the isolated paired TCR alpha and beta chain sequences, or the antigen-binding portion thereof, into host cells to obtain cells that express the paired TCR alpha and beta chain sequences, or the antigen-binding portion thereof.

A further embodiment of the invention provides a pair of TCR alpha and beta chain sequences, or an antigen-binding portion thereof, isolated according to any of the inventive methods described herein.

Still another embodiment of the invention provides an isolated population of cells prepared according to any of the inventive methods described herein.

Further embodiments of the invention provide related pharmaceutical compositions and methods of treating or preventing cancer.

BRIEF DESCRIPTION OF THE SEVERAL VIEWS OF THE DRAWING(S)

FIG. 3A and FIG. 3B are graphs showing the percentage of IFN-γ (A) and IL-2 (B) reads within the total R1 reads measured in 4090 F7 T cells that were co-cultured with TMG-5-pulsed autologous DCs for 4 hr and then subjected to single-cell RNA-seq analysis.

Figure 5A:
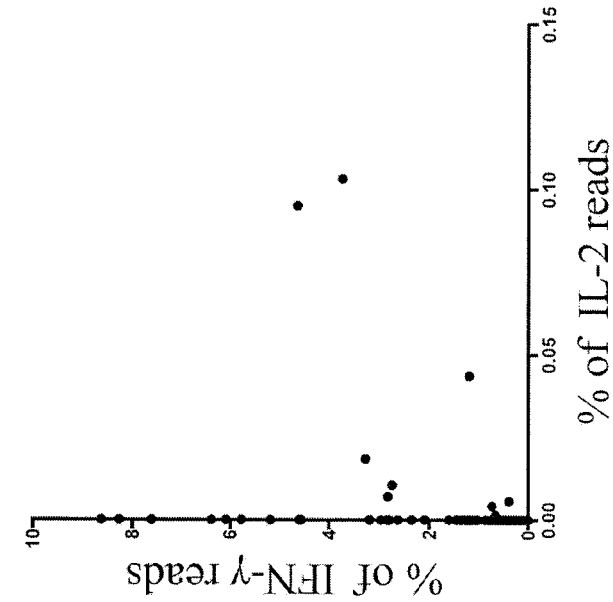
FIG. 5A and FIG. 5B are graphs showing the percentage of IFN-γ (A) and IL-2 (B) reads within the total R1 reads measured in 4112 F5 T cells that were co-cultured with TMG-9-pulsed autologous DCs for 4 hr and then subjected to single-cell RNA-seq analysis.
Figure 5B:
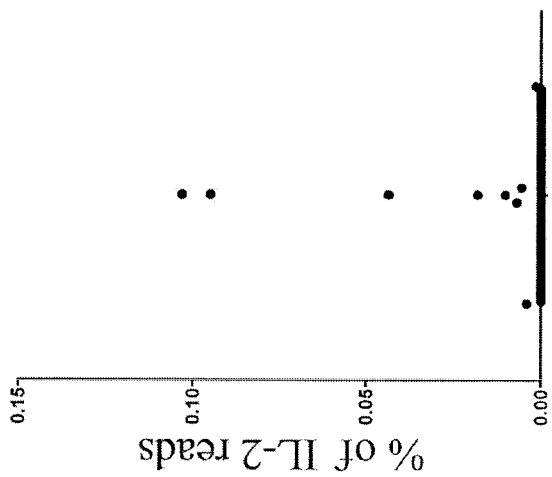
Figure 5C:
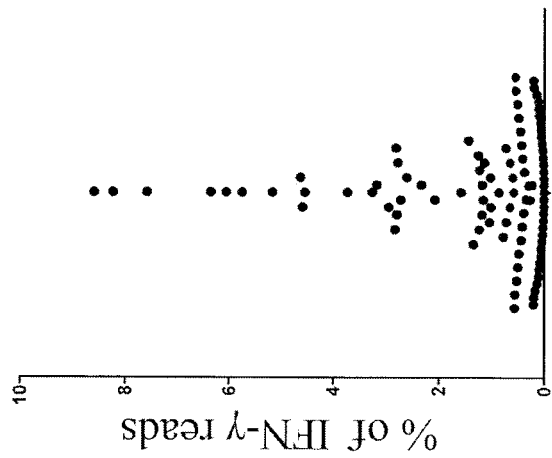
FIG. 5C is a graph showing the percentage of IFN-γ and IL-2 reads within the total R1 reads measured in the 8 single-cells which expressed detectable IL-2 reads in FIG. 5B.
Figures 5D, 5E, 5F:
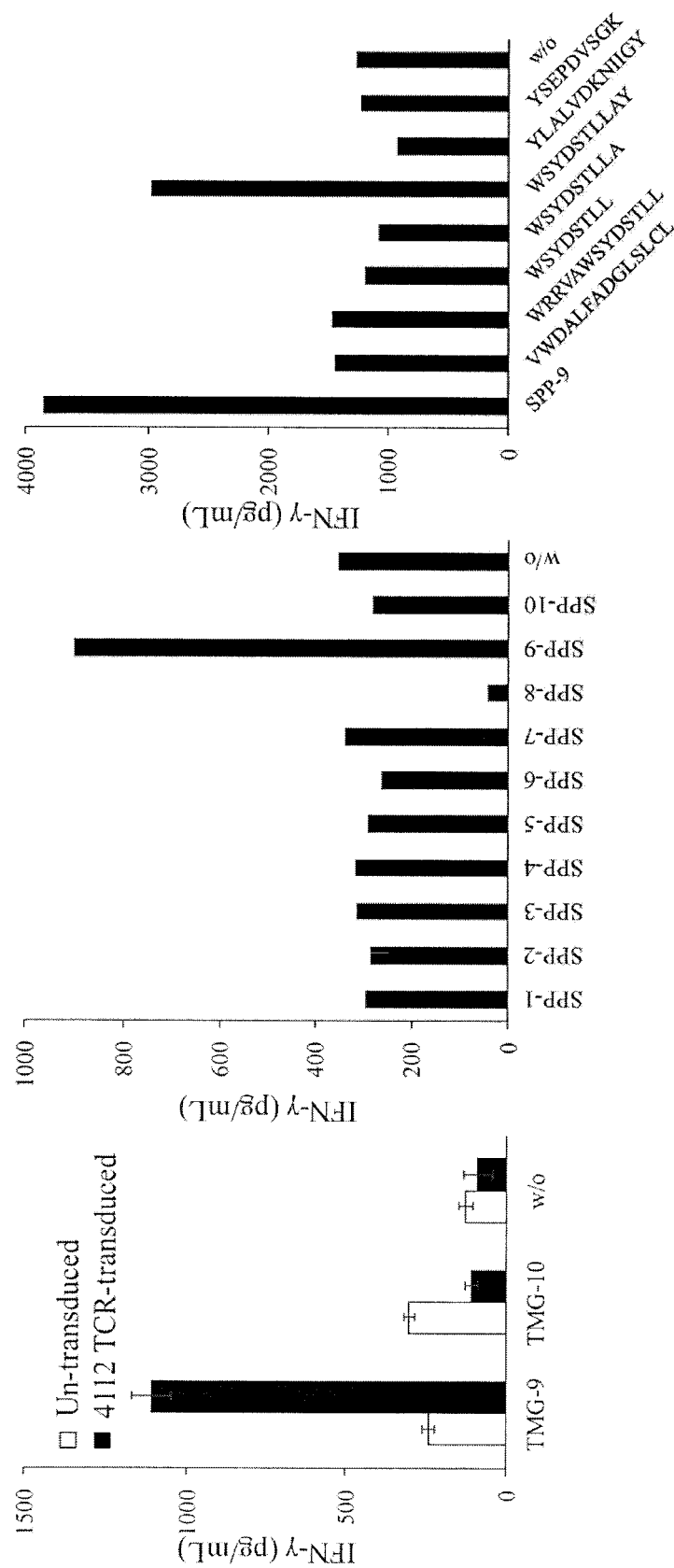
FIG. 5D is a graph showing the amount of IFN-γ (pg/mL) secreted by donor T cells which were untransduced (unshaded bars) or transduced with the 4112 TCR (shaded bars) upon co-culture with DCs pulsed with TMG-9 or TMG-10. DCs pulsed with no peptide ("w/o") served as a negative control.
FIG. 5E is a graph showing the amount of IFN-γ (pg/mL) secreted by 4112 TCR-transduced T cells upon co-culture with EBV-transformed B cells pulsed with one of the indicated pools (SPP-1 to SPP-10) of short peptides. EBV-transformed B cells pulsed with no peptide ("w/o") served as a negative control.

FIG. 5F is a graph showing the amount of IFN-γ (pg/mL) secreted by 4112 TCR-transduced T cells upon co-culture with EBV-transformed B cells pulsed with SPP-9 or one of the indicated short peptides VWDALFADGLSLCL (SEQ ID NO: 18; WRRVAWSYDSTLL (SEQ ID NO: 19 WSYDSTLL (SEQ ID NO: 20; WSYDSTLLA (SEQ ID NO: 21; WSYDSTLLAY (SEQ ID NO: 22; YLALVDKNIIGY (SEQ ID NO: 23; or YSEPDVSGK (SEQ ID NO: 24. EBV-transformed B cells pulsed with no peptide ("w/o") served as a negative control.

Figure 5G:
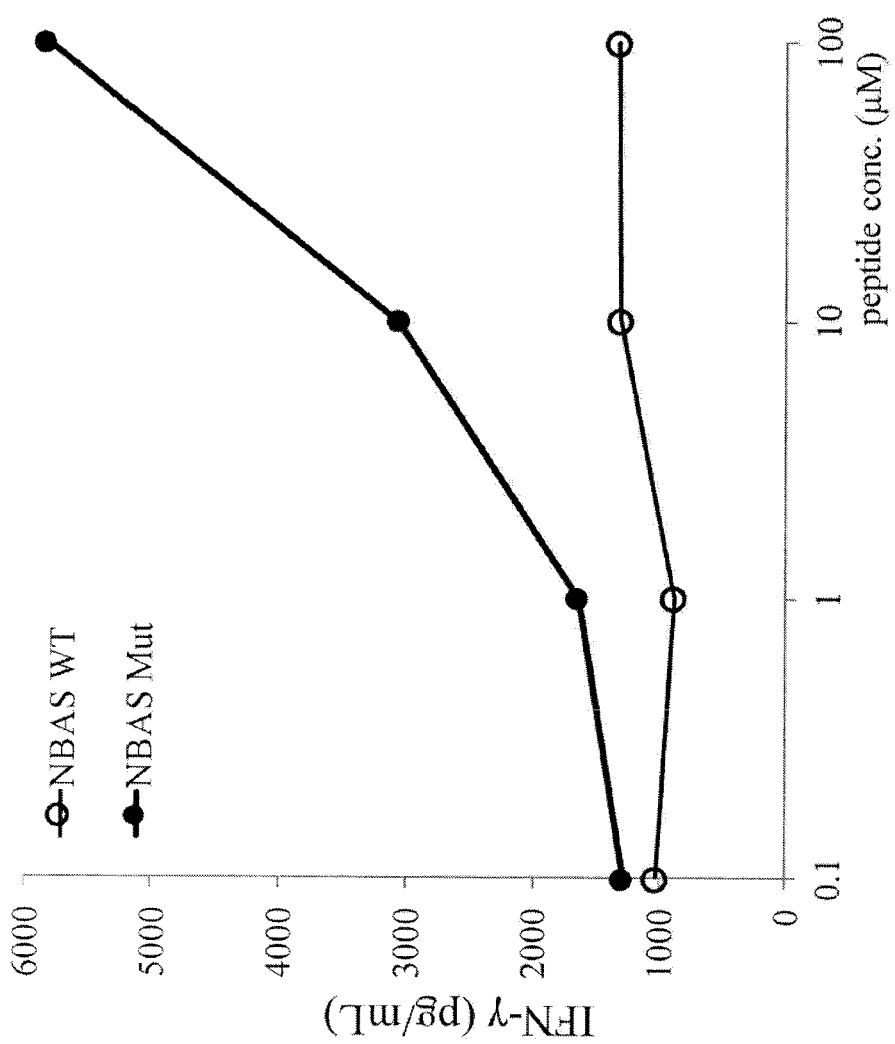

FIG. 5G is a graph showing the amount of IFN-γ (pg/mL) secreted by 4112 TCR-transduced T cells upon co-culture with EBV-transfoinied B cells pulsed with purified mutated (closed circles) NBAS peptide WSYDSTLLAY (C>S) (SEQ ID NO: 4) or its WT (open circles) counterpart.

Figure 6:
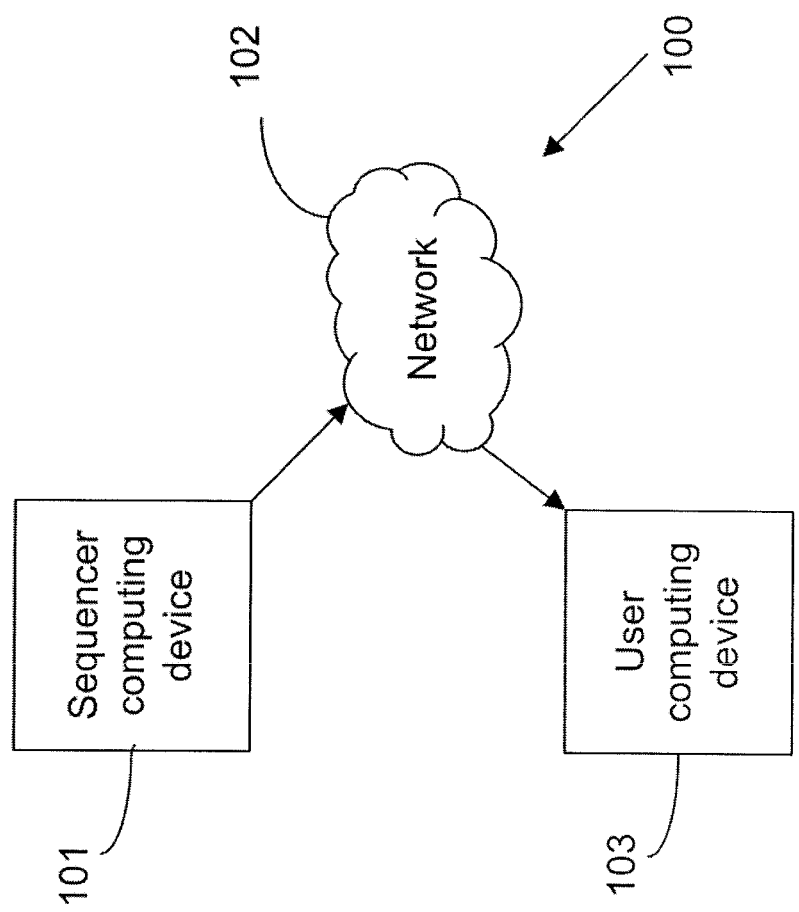

FIG. 6 is a block diagram illustrating a system in accordance with some embodiments of the invention.

Figure 7:
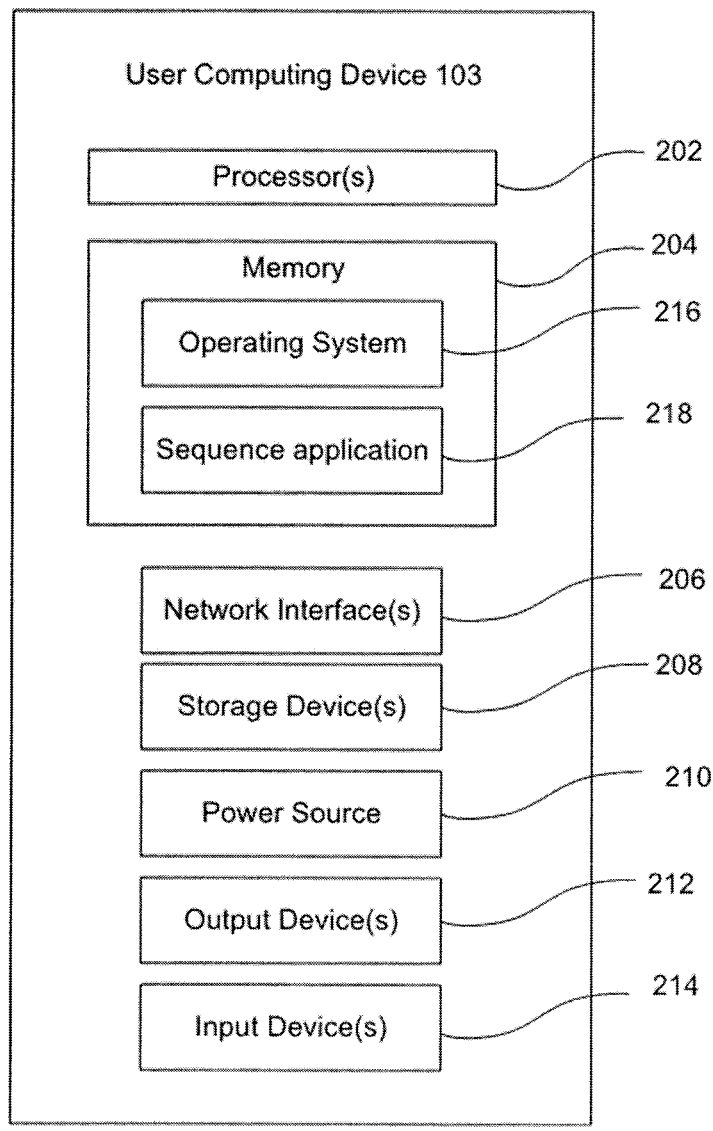

FIG. 7 is a block diagram illustrating components of a computing device according to an embodiment of the invention.

FIG. 8 is a flow diagram of method steps for automatically identifying the T cell receptor (TCR) alpha and beta chain V segment sequences and CDR3 sequences of a TCR having antigenic specificity for a mutated amino acid sequence encoded by a cancer-specific mutation, according to an embodiment of the invention.

FIG. 9A is a graph showing the number of IFN-γ positive spots detected after screening TIL4171F6 T cells against a library of 25-mer long-peptide pools (PP) encoding mutations in an ELISPOT assay. T cells treated with OKT3 antibody served as a positive control. T cells cultured with no peptide pool (w/o) served as a negative control.

FIGS. 9B and 9C are graphs showing the expression of IFN-γ (FPKM (Fragments Per Kilobase of transcript per Million mapped reads)) (FIG. 9B) and IL-2 (FIG. 9C) by TIL 4171 F6 T cells upon co-culture with PP-3-pulsed autologous DCs.

Figure 9D:
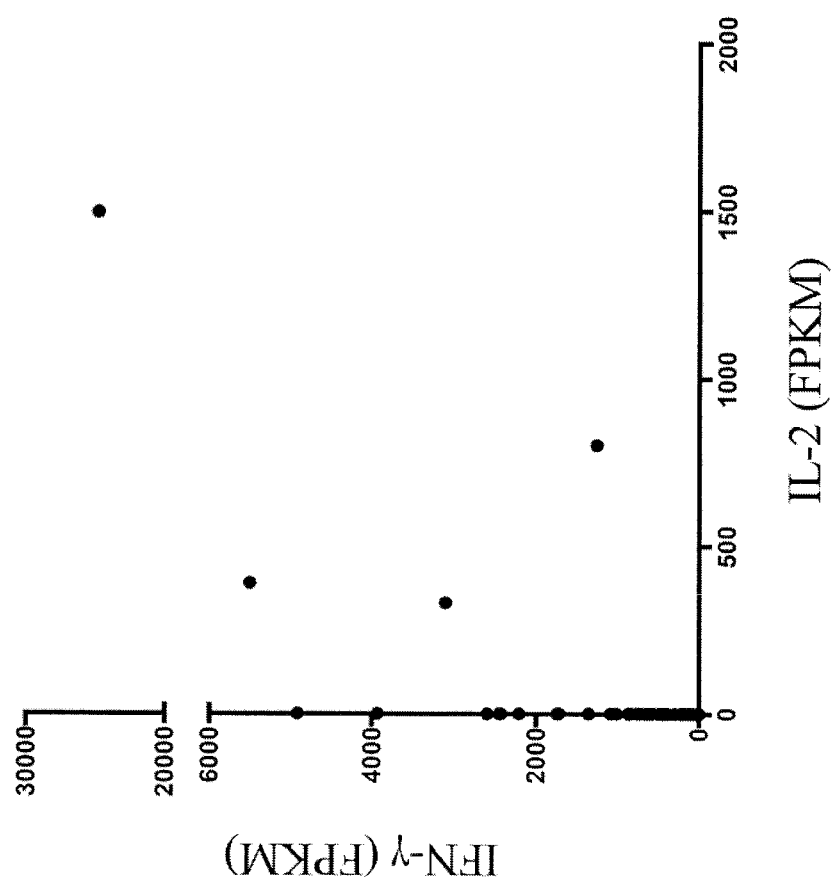

FIG. 9D is a 2-dimensional scatter plot combining the data of FIGS. 9B and 9C showing the relationship of IFN-γ and IL-2 expression in each single cell (each dot represents a single cell).

Figure 9F:
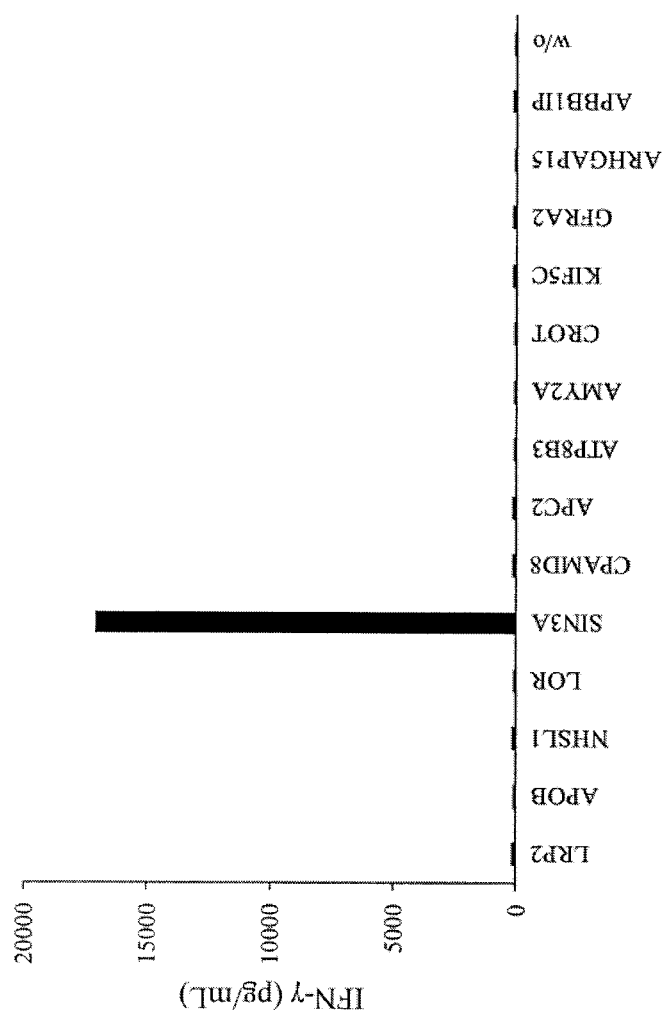
Figure 9E:
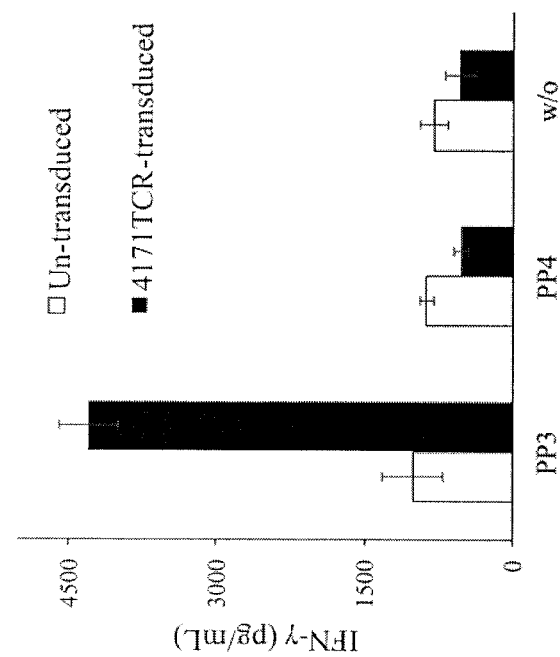

FIG. 9E is a graph showing the amount of IFN-γ (pg/mL) produced following co-culture of untransduced (unshaded bars) or 4171TCR-transduced (shaded bars) cells with PP-pulsed DC. T cells cultured with no peptide pool (w/o) served as a negative control.

FIG. 9F is a graph showing the amount of IFN-γ (pg/mL) produced following co-culture of 4171TCR-transduced T cells with DCs pulsed with the indicated peptides. T cells cultured with no peptide pool (w/o) served as a negative control.

Figure 9G:
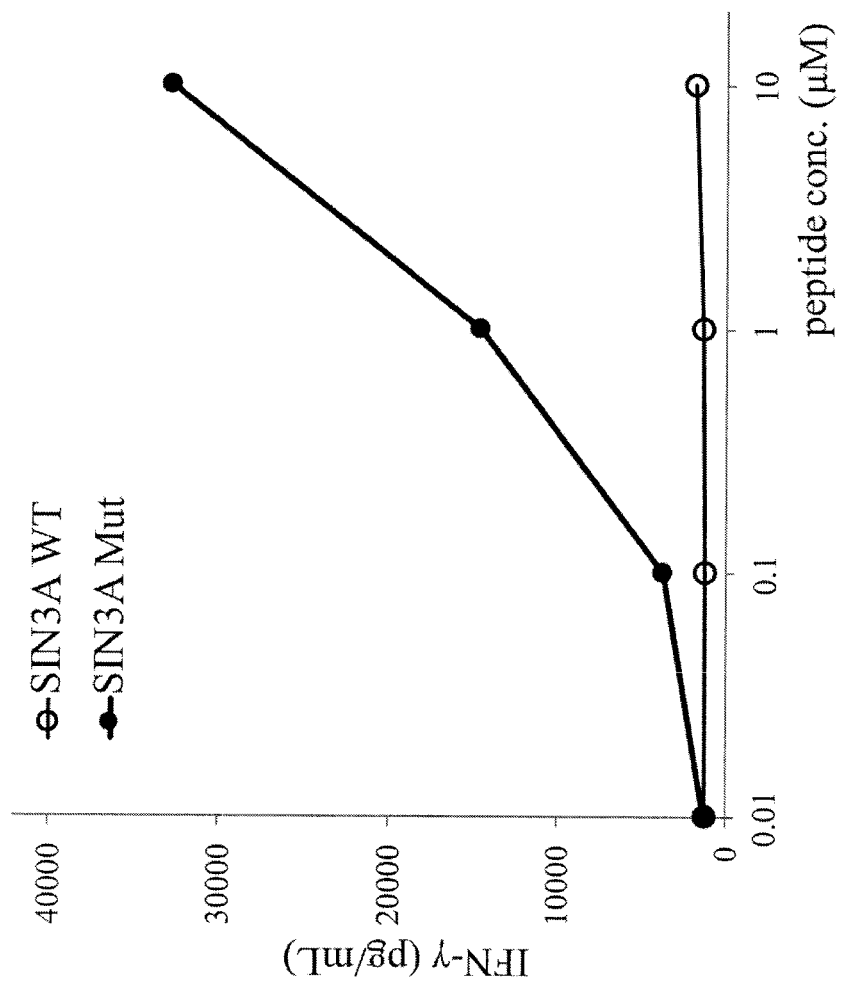

FIG. 9G is a graph showing the amount of IFN-γ (pg/mL) produced following co-culture of 4171TCR-transduced T cells with DCs pulsed with the indicated concentration (μM) of WT (open circles) or mutated (closed circles) SIN3A peptide.

DETAILED DESCRIPTION OF THE INVENTION

An embodiment of the invention provides a method of isolating paired TCR alpha and beta chain sequences, or an antigen-binding portion thereof.

The inventive methods may address any of a variety of different challenges to the identification and isolation of functional TCRs having the desired antigenic specificity. These challenges may include, for example, the large diversity of TCR sequences, the need for TCRα and β chains to be paired correctly in order to provide the desired antigenic specificity, and that up to about one third of mature T cells may express two functional TCRα chains, while only one of the TCRα chains likely has the desired specificity.

The inventive methods may provide any of a variety of advantages. For example, the inventive methods may significantly reduce the time and/or cost that is necessary to isolate and identify the sequence of a TCR that has antigenic specificity for a cancer antigen (e.g., a neoantigen) after a biological sample (e.g., tumor sample) is removed from a patient. After the TCR sequence is isolated and identified, host cells (e.g., autologous T cells) may be transduced with the TCR sequence, the numbers of transduced cells may be expanded, and the expanded numbers of transduced cells may be administered to the patient for the treatment and/or prevention of cancer. The inventive methods may (i) identify both the cancer antigen and the sequence of the TCR which recognizes the cancer antigen and/or (ii) facilitate highly personalized TCR therapy targeting cancer antigens (e.g., neoantigens). Moreover, the inventive methods may be, advantageously, less time-consuming, less laborious, and have a higher success rate as compared to methods of isolating paired TCRα/β sequences using T cell cloning by limiting dilution. The inventive methods may also make it possible to efficiently identify the correct pair of TCR alpha and beta chains in those T cells that have more than one functional TCRα gene. The inventive methods may also identify and isolate paired TCR alpha and beta chain sequences (having the desired antigen specificity) from a highly diverse population of T cells.

The αβ TCR is a heterodimer composed of α and β protein chains. Each chain includes two extracellular domains, the variable (V) region and the constant (C) region, followed by a transmembrane region and a short cytoplasmic tail. The variable domain of each of the TCR α-chain and β-chain have three "complementarity determining regions" (CDR1, CDR2 and CDR3) which contact and recognize a peptide-MHC complexes. In particular, the α and β CDR3s are responsible for recognizing processed antigen. From T cell to T cell, there is an extremely high degree of polymorphism in the amino acid sequences of the CDR3α and CDR3β. This level of polymorphism is necessary for T cells to recognize the wide scope of antigens that confront the immune system. The polymorphism in the amino acid sequences of the CDR3α and CDR3β result from DNA rearrangements within the TCR α and β genes that occur during the maturation of a T cell.

The genes that encode the TCR are made up of cassettes of coding sequence referred to as a "V segment" and a "J segment" in the TCR α-gene and a "V segment", a "D segment," and a "J segment" in the TCR β-chain. Stochastic rearrangement in the genomic DNA results in the juxtaposition of these DNA segments resulting in a functional TCR gene. These rearrangements may be imprecise and junctions of the Vα-Jα and Vβ-Dc-Jβ segments may be highly variable. The CDR3 of the alpha chain is encoded by a portion of the V segment and all of the J segment. The CDR3 of the beta chain is encoded by a portion of the V segment, all of the J segment, and all of the D segment.

The method may comprise isolating, from a biological sample, T cells having antigenic specificity for a mutated amino acid sequence encoded by a cancer-specific mutation. Any suitable biological sample can be used. In an embodiment of the invention, the biological sample is a tumor sample or a sample of peripheral blood. Examples of biological samples that may be used in accordance with invention include, without limitation, tissue from a primary tumors, tissue from the site of metastatic tumors, exudates, effusions, ascites, fractionated peripheral blood cells, bone marrow, peripheral blood buffy coat, and cerebrospinal fluid. As such, the biological sample may be obtained by any suitable means, including, without limitation, aspiration, biopsy, resection, venous puncture, arterial puncture, lumbar spinal puncture, shunts, catheterization, or the placement of a drain.

The T cells which are isolated from the biological sample have antigenic specificity for a mutated amino acid sequence encoded by a cancer-specific mutation. The phrase "antigenic specificity," as used herein, means that a TCR, or the antigen-binding portion thereof, can specifically bind to and immunologically recognize the mutated amino acid sequence encoded by the cancer-specific mutation. The cancer-specific mutation may be any mutation in any gene which encodes a mutated amino acid sequence (also referred to as a "non-silent mutation") and which is expressed in a cancer cell but not in a normal, noncancerous cell. Methods of isolating T cells having antigenic specificity for a mutated amino acid sequence encoded by a cancer-specific mutation are described at, for example, WO 2016/053338 and WO 2016/053339. For example, the isolating of T cells having antigenic specificity for a mutated amino acid sequence encoded by a cancer-specific mutation may comprise: identifying one or more genes in the nucleic acid of a cancer cell of a patient, each gene containing a cancer-specific mutation that encodes a mutated amino acid sequence; inducing autologous antigen presenting cells (APCs) of the patient to present the mutated amino acid sequence; co-culturing autologous T cells of the patient with the autologous APCs that present the mutated amino acid sequence; and selecting the autologous T cells that (a) were co-cultured with the autologous APCs that present the mutated amino acid sequence and (b) have antigenic specificity for the mutated amino acid sequence presented in the context of a major histocompatability complex (MHC) molecule expressed by the patient to provide isolated T cells having antigenic specificity for the mutated amino acid sequence encoded by the cancer-specific mutation.

Once the T cells having antigenic specificity for the mutated amino acid sequence encoded by the cancer-specific mutation have been isolated, the inventive method further comprises co-culturing those isolated T cells with APCs that present the mutated amino acid sequence so that the T cells express one or more T cell activation markers. The APCs may include any cells which present peptide fragments of proteins in association with major histocompatibility complex (MHC) molecules on their cell surface. The APCs may include, for example, any one or more of macrophages, dendritic cells (DCs), langerhans cells, B-lymphocytes, and T-cells. Preferably, the APCs are DCs. Any one or more of a variety of T cell activation markers may be used to identify those T cells having antigenic specificity for the mutated amino acid sequence. Examples of T cell activation markers include, but are not limited to, any one or more of programmed cell death 1 (PD-1), lymphocyte-activation gene 3 (LAG-3), T cell immunoglobulin and mucin domain 3 (TIM-3), 4-1BB, OX40, CD107a, granzyme B, interferon (IFN)-γ, interleukin (IL)-2, tumor necrosis factor alpha (TNF-α), granulocyte/monocyte colony stimulating factor (GM-CSF), IL-4, IL-5, IL-9, IL-10, IL-17, and IL-22.

The method further comprises sorting the co-cultured T cells into separate single T cell samples and isolating mRNA from each separate single T cell sample. The sorting into separate single T cell samples and the isolating of mRNA may be automated. For example, the sorting into separate single T cell samples and the isolating of the mRNA may be carried out using a FLUIDIGM C1 automated single-cell isolation and preparation system (available from Fluidigm, South San Francisco, Calif.). The inventive method may, advantageously, provide any number of separate, single-cell mRNA samples (for example, about 2, about 3, about 4, about 5, about 10, about 11, about 12, about 13, about 14, about 15, about 20, about 25, about 30, about 40, about 50, about 60, about 70, about 80, about 90, about 100, about 150, about 200, about 400, about 600, about 800, about 1000, about 1500, about 2000 or more, or a range defined by any two of the foregoing values). In an embodiment of the invention, the method comprises preparing about 96 separate, single-cell mRNA samples.

In an embodiment of the invention, the method may further comprise labeling the mRNA from each separate single T cell sample with a different tag (e.g., barcode) for each separate single T cell sample. For example, the mRNA from each separate single T cell sample may be labeled using the ILLUMINA NEXTERA XT DNA library preparation kit (available from Illumina, San Diego, Calif.).

The inventive method further comprises sequencing the mRNA from each separate single T cell sample. The sequencing may be carried out in any suitable manner known in the art. Preferred examples of sequencing techniques that may be useful in the inventive methods include Next Generation Sequencing (NGS) (also referred to as "massively parallel sequencing technology" or "deep sequencing") or Third Generation Sequencing. NGS refers to non-Sanger-based high-throughput DNA sequencing technologies. With NGS, millions or billions of DNA strands may be sequenced in parallel, yielding substantially more throughput and minimizing the need for the fragment-cloning methods that are often used in Sanger sequencing of genomes. In NGS, nucleic acid templates may be randomly read in parallel along the entire genome by breaking the entire genome into small pieces. NGS may, advantageously, provide nucleic acid sequence information from each separate single T cell mRNA sample in very short time periods, e.g., within about 1 to about 2 weeks, preferably within about 1 to about 7 days, or most preferably, within less than about 24 hours. Multiple NGS platforms which are commercially available or which are described in the literature can be used in the context of the inventive methods, e.g., those described in Zhang et al., *J. Genet. Genomics,* 38(3): 95-109 (2011) and Voelkerding et al., *Clinical Chemistry,* 55: 641-658 (2009).

Non-limiting examples of NGS technologies and platforms include sequencing-by-synthesis (also known as "pyrosequencing") (as implemented, e.g., using the GS-FLX 454 Genome Sequencer, 454 Life Sciences (Branford, Conn.), ILLUMINA SOLEXA Genome Analyzer (Illumina Inc., San Diego, Calif.), the ILLUMINA HISEQ 2000 Genome Analyzer (Illumina), or the ILLUMINA MISEQ system (Illumina) or as described in, e.g., Ronaghi et al., Science, 281(5375): 363-365 (1998)), sequencing-by-ligation (as implemented, e.g., using the SOLID platform (Life Technologies Corporation, Carlsbad, Calif.) or the POLONATOR G.007 platform (Dover Systems, Salem, N.H.)), single-molecule sequencing (as implemented, e.g., using the PACBIO RS system (Pacific Biosciences (Menlo Park, Calif.) or the HELISCOPE platform (Helicos Biosciences (Cambridge, Mass.)), nano-technology for single-molecule sequencing (as implemented, e.g., using the GRIDON platform of Oxford Nanopore Technologies (Oxford, UK), the hybridization-assisted nano-pore sequencing (HANS) platforms developed by Nabsys (Providence, R.I.), and the ligase-based DNA sequencing platform with DNA nanoball (DNB) technology referred to as probe-anchor ligation (cPAL)), electron microscopy-based technology for single-molecule sequencing, and ion semiconductor sequencing.

In this regard, the sequencing of the mRNA from each separate single T cell sample may comprise producing cDNA from the mRNA and amplifying the cDNA, producing multiple fragments of the amplified cDNA and tagging the multiple fragments, amplifying the tagged, multiple fragments of the cDNA, and sequencing the amplified, tagged multiple fragments of the cDNA. The tagging may comprise adding a nucleotide sequence to each multiple fragment so that the multiple fragments can be distinguished from one another. The sequencing identifies the sequences of each of the multiple fragments of cDNA. The sequence of each of the multiple fragments of cDNA is also referred to as a "read." The sequencing of the mRNA may generate any number of reads. For example, the sequencing of the mRNA may generate about 1,000,000 reads, about 900,000 reads, about 800,000 reads, about 700,000 reads, about 600,000 reads, about 500,000 reads, about 400,000 reads, about 300,000 reads, about 200,000 reads, about 100,000 reads, or more, or a range defined by any two of the foregoing values, for each single T cell sample. In many NGS platforms, there may be two reading directions: one is forward reading (also called "read 1" or "R1"), and the other is reverse reading (also called "read 2" or "R2"). For a cDNA fragment, R1 and R2 may complement each other. In an embodiment of the invention, the method comprises measuring only R1 reads, only R2 reads, or both R1 and R2 reads. R1 may have a higher sequencing quality than R2. Preferably, the method comprises measuring only R1 reads.

The method further comprises aligning the sequences of each of the multiple fragments of cDNA to a known sequence of the one or more T cell activation markers to identify which single T cell sample contained a single T cell which expressed the one or more T cell activation markers. The one or more single T cell(s) which expressed the one or more T cell activation markers following co-culture with the APCs that present the mutated amino acid sequence encoded by a cancer-specific mutation are identified as expressing a TCR which has antigenic specificity for the mutated amino acid sequence encoded by a cancer-specific mutation.

The method further comprises aligning the sequences of each of the multiple fragments of cDNA to a reference TCR sequence database to identify TCR alpha chain variable (V) region sequences and TCR beta chain V region sequences of the multiple fragments of cDNA of each separate single T cell sample which was identified to express one or more T cell activation markers. In this regard, the sequences of each of the multiple fragments of cDNA are aligned against known TCR variable segment sequences in order to identify which cDNA fragments contain all or a portion of the variable segment sequence and to locate the approximate position of the 3' end of the variable segment sequence on the cDNA fragment(s). The 3' end of the variable segment sequence indicates the approximate location of the CDR3.

The reference TCR sequence database may be any suitable reference TCR sequence database. An example of a reference TCR sequence database may include sequences obtained from the international IMMUNOGENETICS information system (IMGT) database (//www.imgt.org), described in Lefranc et al., *Nucleic Acids Res.*, 43: D413-422 (2015). The aligning of the sequences of each of the multiple fragments of cDNA to the reference TCR sequence database may be carried out, for example, using the Burrows-Wheeler Aligner (BWA) software package (//bio-bwa.sourceforge.net/), described in Li et al., *Bioinformatics*, 25: 1754-60 (2009) and Li et al., *Bioinformatics*, 26(5): 589-95 (2010).

The method further comprises identifying TCR complementarity determining region 3 (CDR3) sequences in the multiple fragments of cDNA containing the identified TCR alpha chain V segment sequences and in the multiple fragments of cDNA containing the identified TCR beta chain V segment sequences. The CDR3 region sequence may be identified in any suitable manner. In an embodiment of the invention, identifying TCR CDR3 sequences is carried out by identifying cDNA sequences which encode conserved amino acid residues positioned near the C-terminus of the amino acid sequence which is encoded by the V segment of the alpha and beta chains. For example, identifying a TCR CDR3 sequence may be carried out by identifying any cDNA sequence(s) which encodes the amino acid sequence motif of (SEQ ID NO: 5)
$YX_1CX_2X_3X_4X_5X_6X_7X_8X_9X_{10}X_{11}X_{12}X_{13}X_{14}X_{15}X_{16}X_{17}X_{18}X_{19}X_{20}X_{21}X_{22}$, wherein each of $X_1$-$X_9$ is any naturally occurring amino acid, each of $X_{10}$-$X_{21}$ is no amino acid or is any naturally occurring amino acid, and $X_{22}$ is phenylalanine or tryptophan. The amino acid sequence motif of SEQ ID NO: 5 is a conserved amino acid sequence motif positioned near the C-terminus of the amino acid sequence encoded by the V segment.

In an embodiment of the invention, the method further comprises identifying the TCR alpha chain constant (C) region sequence of the highest number of multiple fragments of cDNA collected and the TCR beta chain C region sequence of the highest number of multiple fragments of cDNA collected. Optionally, the method further comprises identifying the TCR alpha chain C region sequence of the second highest number of multiple fragments of cDNA collected. A TCR alpha chain has one possible constant region amino acid sequence. A TCR beta chain has one of two possible constant region amino acid sequences.

The method further comprises counting the number of multiple fragments of cDNA which share the same alpha chain CDR3 amino acid sequence and the number of multiple fragments of cDNA which share the same beta chain CDR3 amino acid sequence.

The method further comprises collecting the highest number of multiple fragments of cDNA which encode the same alpha chain CDR3 sequence, the highest number of multiple fragments of cDNA which encode the same beta chain CDR3 sequence and, optionally, the second highest number of multiple fragments of cDNA which encode the same alpha chain CDR3 sequence to identify TCR alpha and beta chain CDR3 sequences. The alpha chain CDR3 sequence encoded by the second highest number of multiple fragments of cDNA is different from the alpha chain CDR3 sequence encoded by the highest number of multiple fragments of cDNA. The CDR3 sequences identified may include the beta chain CDR3 sequence and the alpha chain CDR3 sequence of the TCR having antigenic specificity for the mutated amino acid sequence encoded by the cancer-specific mutation and, optionally, an additional alpha chain CDR3 sequence expressed by the T cell but which does not pair with the beta chain CDR3 sequence to form the TCR having antigenic specificity for the mutated amino acid sequence encoded by the cancer-specific mutation. It is estimated that about a third of mature T cells may express two TCR alpha chains. Only one of the expressed alpha chains will pair with the expressed TCR beta chain to provide a TCR which has antigenic specificity for the amino acid sequence encoded by the cancer-specific mutation.

The method further comprises identifying the TCR alpha chain V segment sequence of the highest number of multiple fragments of cDNA collected, the TCR beta chain V segment sequence of the highest number of multiple fragments of cDNA collected, and, optionally, the TCR alpha chain V segment sequence of the second highest number of multiple fragments of cDNA collected to identify TCR alpha and beta chain V segment sequences. The number of multiple fragments of cDNA which encode the CDR3 sequence of the dominant TCR expressed by a single, activated T cell will outnumber the number of fragments of cDNA which encode any other TCR CDR3 sequence which may be present due to contamination by a factor of about 10 to about 100. The source of the contamination may be nearby single-cell samples or unknown sources. The dominant TCR expressed by the single T cell, which expressed one or more T cell activation markers in response to co-culture with APCs that present the mutated amino acid sequence, is a TCR which has antigenic specificity for the mutated amino acid sequence encoded by the cancer-specific mutation.

The method further comprises assembling one or more nucleotide sequences encoding a TCR alpha chain comprising the identified TCR alpha chain V segment sequence identified and the collected TCR alpha chain CDR3 sequence and a TCR beta chain comprising the identified TCR beta chain V segment sequence and the collected TCR beta chain CDR3 sequence. The various multiple fragments of cDNA which encode the same CDR3 sequence may be of various lengths and may overlap with one another. By aligning the various multiple fragments of cDNA which encode the same alpha chain CDR3 sequence of various lengths with one another, the sequence of the entire V segment, J segment, and, optionally, the constant region, of the dominant TCR alpha chain can be determined. By aligning the various multiple fragments of cDNA which encode the same beta chain CDR3 sequence of various lengths with one another, the sequence of the entire V segment, J segment, D segment, and, optionally, the constant region, of the dominant TCR beta chain can be determined. A nucleotide sequence encoding the entire V segment, J segment, and, optionally, the constant region, of the dominant TCR alpha chain and a nucleotide sequence encoding the entire V segment, J segment, D segment, and, optionally, the constant region, of the dominant TCR beta chain can be assembled using routine techniques. Isolated paired TCR alpha and beta chain sequences, or an antigen-binding portion thereof, may be produced.

In an embodiment of the invention, the assembling of one or more nucleotide sequences comprises assembling a TCR alpha chain comprising the TCR alpha chain V segment sequence identified in the sample, the TCR alpha chain C region sequence identified in the sample, and the TCR alpha chain CDR3 sequence collected and assembling a TCR beta chain comprising the TCR beta chain V segment sequence identified in the sample, the TCR beta chain C region sequence identified in the sample, and the TCR beta chain CDR3 sequence collected. In this regard, the nucleotide sequences assembled may comprise an endogenous C region sequence.

In an embodiment of the invention, the assembling of one or more nucleotide sequences comprises assembling a TCR alpha chain comprising the TCR alpha chain V segment sequence identified in the sample, an exogenous TCR alpha chain C region sequence, and the TCR alpha chain CDR3 sequence collected and assembling a TCR beta chain comprising the TCR beta chain V segment sequence identified in the sample, an exogenous TCR beta chain C region sequence, and the TCR beta chain CDR3 sequence collected. An exogenous C region sequence is a C region sequence that is not native to (not naturally-occurring on) the T cell. In this regard, the isolated paired TCR alpha and beta chain sequence, or an antigen-binding portion thereof, produced by the method may be a chimeric or hybrid TCR comprised of amino acid sequences derived from TCRs from two different mammalian species. For example, the TCR can comprise a variable region derived from a human TCR and a constant region of a mouse TCR such that the TCR is "murinized." Methods of making chimeric or hybrid TCRs are described in, for example, Cohen et al., *Cancer Res.*, 66: 8878-8886 (2006); Cohen et al., *Cancer Res.*, 67: 3898-3903 (2007); and Haga-Friedman et al., *J. Immunol.*, 188: 5538-5546 (2012)).

A single T cell typically expresses one TCR beta chain and one or two TCR alpha chains. The presence of more than one TCR beta chain in a single sample may be the result of imperfect sorting of the T cells into separate T cell samples. Imperfect sorting may result in two or more T cells inadvertently being included in one sample. If a single sample is found to express more than one TCR beta chain, that sample may be eliminated from subsequent analysis.

As discussed above, it is estimated that about a third of mature T cells may express two TCR alpha chains. Only one of the expressed alpha chains will pair with the expressed TCR beta chain to provide a TCR which has antigenic specificity for the amino acid sequence encoded by the cancer-specific mutation. In order to determine which TCR alpha chain pairs with the TCR beta chain to provide the desired specificity, the method may comprise assembling a first nucleotide sequence encoding a first TCR alpha chain comprising the first TCR alpha chain V segment sequence of the highest number of multiple fragments of cDNA identified as described herein and the first TCR alpha chain CDR3 sequence collected as described herein and a TCR beta chain comprising the TCR beta chain V segment sequence identified as described herein and the TCR beta chain CDR3 sequence collected as described herein. The method may optionally further comprise assembling a second one or more nucleotide sequences encoding: a second TCR alpha chain comprising the TCR alpha chain V segment sequence of the second highest number of multiple fragments of cDNA identified and the TCR alpha chain CDR3 sequence of the second highest number of multiple fragments of cDNA collected and the TCR beta chain comprising the TCR beta chain V segment sequence identified and the TCR beta chain CDR3 sequence collected.

The method may further comprise independently introducing the first and second nucleotide sequences into first and second populations of host cells, respectively, and independently co-culturing the first and second populations of host cells with APCs that present the mutated amino acid sequence encoded by a cancer-specific mutation. The method may further comprise selecting the population of host cells that (a) were co-cultured with the APCs that present the mutated amino acid sequence and (b) have antigenic specificity for the mutated amino acid sequence. The co-cultured population of host cells that has antigenic specificity for the mutated amino acid sequence will express the TCR alpha chain which, together with the TCR beta chain, provides the desired specificity.

Cells which have antigenic specificity for the mutated amino acid sequence may be identified by any suitable means known in the art. For example, cells which have antigenic specificity for the mutated amino acid sequence may be identified on the basis of expression of one or more T cell activation markers and/or one or more cytokines, as described in, for example, WO 2016/053338 and WO 2016/053339. The T cell activation markers may be as described herein with respect to other aspects of the invention. The cytokine may comprise any cytokine the secretion of which by a T cell is characteristic of T cell activation (e.g., a TCR expressed by the T cells specifically binding to and immunologically recognizing the mutated amino acid sequence). Non-limiting examples of cytokines, the secretion of which is characteristic of T cell activation, include IFN-γ, IL-2, granzyme B, and tumor necrosis factor alpha (TNF-α), granulocyte/monocyte colony stimulating factor (GM-CSF), IL-4, IL-5, IL-9, IL-10, IL-17, and IL-22.

In some embodiments, one or more steps of the inventive methods are carried out using a software system. In this regard, an embodiment of the invention provides a method of automatically identifying the TCR alpha and beta chain V segment sequences and CDR3 sequences of a TCR having antigenic specificity for a mutated amino acid sequence encoded by a cancer-specific mutation.

FIG. 6 is a block diagram of a system 100 in accordance with certain embodiments of the invention. The system 100 may include one or more sequencer computer device(s) 101, a user computing device 103, and a network connection 102 between the user computing device 103 and the sequencer computing device 101. The sequencer computing device 101 may be any system which is capable of sequencing the mRNA from each separate single T cell sample. Examples of sequencer computing devices 101 may include any of the NGS technologies and platforms described herein with respect to other aspects of the invention.

The user computing device 101 can be any type of communication device that supports network communication, including a personal computer, a laptop computer, or a personal digital assistant (PDA), etc. In some embodiments, the user computing device 101 can support multiple types of networks. For example, the user computing device 101 may have wired or wireless network connectivity using IP (Internet Protocol) or may have mobile network connectivity allowing over cellular and data networks.

As described in greater detail herein, user computing device 103 is used to capture the sequences of each of the multiple fragments of cDNA provided by the sequencer computing device 101. The sequences may be transmitted over a network connection 102. An example of a network connection 102 is shared disk space.

FIG. 7 is a block diagram of basic functional components for a computing device 103 according to some aspects of the invention. In the illustrated embodiment of FIG. 7, the computing device 103 includes one or more processors 202, memory 204, network interfaces 206, storage devices 208, power source 210, one or more output devices 212, one or more input devices 214, and software modules—operating system 216 and a sequence application 218—stored in memory 204. The software modules are provided as being contained in memory 204, but in certain embodiments, the software modules are contained in storage devices 208 or a combination of memory 204 and storage devices 208. Each of the components including the processor 202, memory 204, network interfaces 206, storage devices 208, power source 210, output devices 212, input devices 214, operating system 216, and the sequence application 218, is interconnected physically, communicatively, and/or operatively for inter-component communications.

As illustrated, processor 202 is configured to implement functionality and/or process instructions for execution within client device 103. For example, processor 202 executes instructions stored in memory 204 or instructions stored on a storage device 208. Memory 204, which may be a non-transient, computer-readable storage medium, is configured to store information within client device 103 during operation. In some embodiments, memory 204 includes a temporary memory, an area for information not to be maintained when the client device 103 is turned off. Examples of such temporary memory include volatile memories such as random access memories (RAM), dynamic random access memories (DRAM), and static random access memories (SRAM). Memory 204 also maintains program instructions for execution by the processor 202.

Storage device 208 also includes one or more non-transient computer-readable storage media. The storage device 208 is generally configured to store larger amounts of information than memory 204. The storage device 208 may further be configured for long-term storage of information. In some embodiments, the storage device 208 includes non-volatile storage elements. Non-limiting examples of non-volatile storage elements include magnetic hard discs, optical discs, floppy discs, flash memories, or forms of electrically programmable memories (EPROM) or electrically erasable and programmable (EEPROM) memories.

User computing device 103 may use network interface 206 to communicate with external sequencer computing devices 101 via one or more networks 102 (see FIG. 6), and other types of networks through which a communication with the user computing device 103 may be established. Network interface 206 may be a network interface card, such as an ETHERNET card, an optical transceiver, a radio frequency transceiver, or any other type of device that can send and receive information. Other non-limiting examples of network interfaces include Bluetooth®, 3G and Wi-Fi radios in client computing devices, and Universal Serial Bus (USB).

User computing device 103 includes one or more power sources 210 to provide power to the device. Non-limiting examples of power source 210 include single-use power sources, rechargeable power sources, and/or power sources developed from nickel-cadmium, lithium-ion, or other suitable material.

One or more output devices 212 are also included in user computing device 103. Output devices 212 are configured to provide output to a user using tactile, audio, and/or video stimuli. Output device 212 may include a display screen (part of the presence-sensitive screen), a sound card, a video graphics adapter card, or any other type of device for converting a signal into an appropriate form understandable to humans or machines. Additional examples of output device 212 include a speaker such as headphones, a cathode ray tube (CRT) monitor, a liquid crystal display (LCD), or any other type of device that can generate intelligible output to a user.

The user computing device includes one or more input devices 214. Input devices 214 are configured to receive input from a user or a surrounding environment of the user through tactile, audio, and/or video feedback. Non-limiting examples of input device 214 include a photo and video camera, presence-sensitive screen, a mouse, a keyboard, a voice responsive system, microphone or any other type of input device. In some examples, a presence-sensitive screen includes a touch-sensitive screen.

The client device 103 includes an operating system 216. The operating system 216 controls operations of the components of the client device 103. For example, the operating system 216 facilitates the interaction of the processor(s) 202, memory 204, network interface 206, storage device(s) 208, input device 214, output device 212, and power source 210.

As described in greater detail herein, the user computing device may use sequence application 218 to capture the sequences of the multiple fragments of cDNA of the single T cell(s) identified to express one or more T cell activation markers following co-culture with APCs that present the mutated amino acid sequence. In some embodiments, the sequence application 218 may interface with and receive inputs from a sequencer computing device. In some embodiments, the user may download the sequences of the multiple fragments of cDNA of a single identified T cell from the sequencer computing device 101 to a removable disk such as, for example, a USB flash drive. The user computing device may obtain the sequences of the multiple fragments of cDNA of a single identified T cell from the removable disk.

The user computing device 103 may include software stored in a memory and executed by a processor to identify the TCR alpha and beta chain V segment sequences and CDR3 sequences of a TCR having antigenic specificity for a mutated amino acid sequence encoded by a cancer-specific mutation, as described herein with respect to other aspects of the invention.

FIG. 8 is a flow diagram of method steps for automatically identifying the TCR alpha and beta chain V segment sequences and CDR3 sequences of a TCR having antigenic specificity for a mutated amino acid sequence encoded by a cancer-specific mutation. As shown, the method 400 begins at step 402, where a user computing device 103 receives the sequences of the multiple fragments of cDNA of the single T cell(s) which was/were identified to express one or more T cell activation markers following co-culture with APCs that present the mutated amino acid sequence encoded by the cancer-specific mutation. The method may comprise receiving the sequences of the multiple fragments of cDNA at the computing device over an electronic network or via a removable disk (e.g., USB drive).

At step 403, the user computing device 103 performs computerized alignment of the sequences of each of the multiple fragments of cDNA to a reference TCR sequence database to identify TCR alpha chain V segment sequences and TCR beta chain V segment sequences of the multiple fragments of cDNA of the single T cell identified to express one or more T cell activation markers following co-culture with APCs that present the mutated amino acid sequence encoded by the cancer-specific mutation.

At step 404, the user computing device 103 performs computerized identification of TCR CDR3 sequences in the multiple fragments of cDNA containing the identified TCR alpha chain V segment sequences and in the multiple fragments of cDNA containing the identified TCR beta chain V segment sequences.

At step 405, the user computing device 103 performs computerized counting of the number of multiple fragments of cDNA which share the same alpha chain CDR3 amino acid sequence and the number of multiple fragments of cDNA which share the same beta chain CDR3 amino acid sequence.

At step 406, the user computing device performs computerized collecting of the highest number of multiple fragments of cDNA which encode the same alpha chain CDR3 sequence, the highest number of multiple fragments of cDNA which encode the same beta chain CDR3 sequence and, optionally, the second highest number of multiple fragments of cDNA which encode the same alpha chain CDR3 sequence, wherein the alpha chain CDR3 sequence encoded by the second highest number of multiple fragments of cDNA is different from the alpha chain CDR3 sequence encoded by the highest number of multiple fragments of cDNA to identify the TCR alpha and beta chain CDR3 sequences.

At step 407, the user computing device 103 performs computerized identification of the TCR alpha chain V segment sequence of the highest number of multiple fragments of cDNA collected, the TCR beta chain V segment sequence of the highest number of multiple fragments of cDNA collected and, optionally, the TCR alpha chain V segment sequence of the second highest number of multiple fragments of cDNA collected to identify the TCR alpha and beta chain V segment sequences.

Another embodiment of the invention provides a pair of TCR alpha and beta chain sequences, or an antigen-binding portion thereof, isolated according to any of the methods described herein with respect to other aspects of the invention. An embodiment of the invention provides an isolated TCR comprising two polypeptides (i.e., polypeptide chains), such as an alpha (α) chain of a TCR and a beta (β) chain of a TCR. The polypeptides of the inventive isolated pairs of TCR alpha and beta chain sequences (also referred to herein as "the inventive TCR(s)"), or the antigen-binding portion thereof, can comprise any amino acid sequence, provided that the TCR, or the antigen-binding portion thereof, has antigenic specificity for the mutated amino acid sequence encoded by the cancer-specific mutation.

The "the antigen-binding portion" of the isolated pair of TCR alpha and beta chain sequences, as used herein, refers to any portion comprising contiguous amino acids of the TCR of which it is a part, provided that the antigen-binding portion specifically binds to the mutated amino acid sequence encoded by the cancer-specific mutation as described herein with respect to other aspects of the invention. The term "antigen-binding portion" refers to any part or fragment of the TCR isolated by the inventive methods, which part or fragment retains the biological activity of the TCR of which it is a part (the parent TCR). Antigen-binding portions encompass, for example, those parts of a TCR that retain the ability to specifically bind to the mutated amino acid sequence, or detect, treat, or prevent cancer, to a similar extent, the same extent, or to a higher extent, as compared to the parent TCR. In reference to the parent TCR, the antigen-binding portion can comprise, for instance, about 10%, 25%, 30%, 50%, 68%, 80%, 90%, 95%, or more, of the parent TCR.

The antigen-binding portion can comprise an antigen-binding portion of either or both of the α and β chains of the TCR isolated by the inventive methods, such as a portion comprising one or more of the complementarity determining region (CDR)1, CDR2, and CDR3 of the variable region(s) of the α chain and/or β chain of the TCR isolated by the inventive methods. In an embodiment of the invention, the antigen-binding portion can comprise the amino acid sequence of the CDR1 of the α chain (CDR1α), the CDR2 of the α chain (CDR2α), the CDR3 of the α chain (CDR3α), the CDR1 of the β chain (CDR1β), the CDR2 of the β chain (CDR2β), the CDR3 of the β chain (CDR3β), or any combination thereof. Preferably, the antigen-binding portion comprises the amino acid sequences of CDR1α, CDR2α, and CDR3α; the amino acid sequences of CDR1β, CDR2β, and CDR3β; or the amino acid sequences of all of CDR1α, CDR2α, CDR3α, CDR1β, CDR2β, and CDR3β of the TCR isolated by the inventive methods.

In an embodiment of the invention, the antigen-binding portion can comprise, for instance, the variable region of the TCR isolated by the inventive methods comprising a combination of the CDR regions set forth above, for example, all six CDR regions set forth above. In this regard, the antigen-binding portion can comprise the amino acid sequence of the variable region of the α chain (Vα), the amino acid sequence of the variable region of the β chain (Vβ), or the amino acid sequences of both of the Vα and Vβ of the TCR isolated by the inventive methods.

In an embodiment of the invention, the antigen-binding portion may comprise a combination of a variable region and a constant region. In this regard, the antigen-binding portion can comprise the entire length of the α or β chain, or both of the α and β chains, of the TCR isolated by the inventive methods.

The isolated paired TCR alpha and beta chain sequences, or the antigen-binding portion thereof, isolated by the inventive methods may be useful for preparing cells for adoptive cell therapies. In this regard, another embodiment of the method provides a method of preparing a population of cells that express paired TCR alpha and beta chain sequences, or an antigen-binding portion thereof. The method may comprise isolating paired TCR alpha and beta chain sequences, or an antigen-binding portion thereof, according to any of the methods described herein with respect to other aspects of the invention.

The method may further comprise introducing the nucleotide sequence encoding the isolated paired TCR alpha and beta chain sequences, or the antigen-binding portion thereof, into host cells to obtain cells that express the paired TCR alpha and beta chain sequences, or the antigen-binding portion thereof. In this regard, the method may comprise cloning the nucleotide sequence that encodes the isolated paired TCR alpha and beta chain sequences, or the antigen-binding portion thereof, into a recombinant expression vector using established molecular cloning techniques as described in, e.g., Green et al. (Eds.), *Molecular Cloning: A Laboratory Manual*, Cold Spring Harbor Laboratory Press; 4th Ed. (2012). For purposes herein, the term "recombinant expression vector" means a genetically-modified oligonucleotide or polynucleotide construct that permits the expression of an mRNA, protein, polypeptide, or peptide by a host cell, when the construct comprises a nucleotide sequence encoding the mRNA, protein, polypeptide, or peptide, and the vector is contacted with the cell under conditions sufficient to have the mRNA, protein, polypeptide, or peptide expressed by the cell. The vectors of the invention are not naturally-occurring as a whole. However, parts of the vectors can be naturally-occurring. The recombinant expression vectors can comprise any type of nucleotides, including, but not limited to DNA and RNA, which can be single-stranded or double-stranded, synthesized or obtained in part from natural sources, and which can contain natural, non-natural or altered nucleotides. The recombinant expression vectors can comprise naturally-occurring, non-naturally-occurring internucleotide linkages, or both types of linkages. Preferably, the non-naturally occurring or altered nucleotides or internucleotide linkages do not hinder the transcription or replication of the vector.

The recombinant expression vector of the invention can be any suitable recombinant expression vector, and can be used to transform or transfect any suitable host cell. Suitable vectors include those designed for propagation and expansion or for expression or both, such as plasmids and viruses. The vector can be selected from the group consisting of transposon/transposase, the pUC series (Fermentas Life Sciences), the pBluescript series (Stratagene, LaJolla, Calif.), the pET series (Novagen, Madison, Wis.), the pGEX series (Pharmacia Biotech, Uppsala, Sweden), and the pEX series (Clontech, Palo Alto, Calif.). Bacteriophage vectors, such as λGT10, λGT11, λZapII (Stratagene), λEMBL4, and λNM1149, also can be used. Examples of plant expression vectors include pBI01, pBI101.2, pBI101.3, pBI121 and pBIN19 (Clontech). Examples of animal expression vectors include pEUK-Cl, pMAM and pMAMneo (Clontech). Preferably, the recombinant expression vector is a viral vector, e.g., a retroviral vector.

Introducing the nucleotide sequence (e.g., a recombinant expression vector) encoding the isolated paired TCR alpha and beta chain sequences, or the antigen-binding portion thereof, into host cells may be carried out in any of a variety of different ways known in the art as described in, e.g., Green et al. supra. Non-limiting examples of techniques that are useful for introducing a nucleotide sequence into host cells include transformation, transduction, transfection, and electroporation.

In an embodiment of the invention, the method comprises introducing the nucleotide sequence encoding the isolated paired TCR alpha and beta chain sequences, or the antigen-binding portion thereof, into host cells that are autologous to the patient who provided the biological sample. In this regard, the TCRs, or the antigen-binding portions thereof, identified and isolated by the inventive methods may be personalized to each patient. However, in another embodiment, the inventive methods may identify and isolate TCRs, or the antigen-binding portions thereof, that have antigenic specificity against a mutated amino acid sequence that is encoded by a recurrent (also referred to as "hot-spot") cancer-specific mutation. In this regard, the method may comprise introducing the nucleotide sequence encoding the isolated paired TCR alpha and beta chain sequences, or the antigen-binding portion thereof, into host cells that are allogeneic to the patient. For example, the method may comprise introducing the nucleotide sequence encoding the isolated paired TCR alpha and beta chain sequences, or the antigen-binding portion thereof, into the host cells of another patient whose tumors express the same mutation in the context of the same MHC molecule as the patient who originally expressed the TCR.

In an embodiment of the invention, the host cells are peripheral blood mononuclear cells (PBMC). The PBMC may include T cells. T cells can be obtained from numerous sources in the patient, including but not limited to tumor, blood, bone marrow, lymph node, the thymus, or other tissues or fluids. The T cells can include any type of T cell and can be of any developmental stage, including but not limited to, CD4+/CD8+ double positive T cells, CD4+ helper T cells, e.g., Th1 and Th2 cells, CD8+ T cells (e.g., cytotoxic T cells), tumor infiltrating cells (e.g., tumor infiltrating lymphocytes (TIL)), peripheral blood T cells, memory T cells, naïve T cells, and the like. The T cells may be CD8+ T cells, CD4+ T cells, or both CD4+ and CD8+ T cells.

Without being bound to a particular theory or mechanism, it is believed that less differentiated, "younger" T cells may be associated with any one or more of greater in vivo persistence, proliferation, and antitumor activity as compared to more differentiated, "older" T cells. Accordingly, the inventive methods may, advantageously, identify and isolate paired TCR alpha and beta chain sequences, or an antigen-binding portion thereof, that has antigenic specificity for the mutated amino acid sequence and introduce the paired TCR alpha and beta chain sequences, or an antigen-binding portion thereof, into "younger" T cells that may provide any one or more of greater in vivo persistence, proliferation, and antitumor activity as compared to "older" T cells (e.g., effector cells in a patient's tumor) from which the TCR, or the antigen-binding portion thereof, may have been isolated.

In an embodiment of the invention, the method further comprises expanding the numbers of host cells into which the TCR, or the antigen-binding portion thereof has been introduced. Expansion of the numbers of cells can be accomplished by any of a number of methods as are known in the art as described in, for example, U.S. Pat. Nos. 8,034,334; 8,383,099; U.S. Patent Application Publication No. 2012/0244133; Dudley et al., J. Immunother., 26:332-42 (2003); and Riddell et al., J. Immunol. Methods, 128:189-201 (1990). In an embodiment, expansion of the numbers of cells is carried out by culturing the T cells with OKT3 antibody, IL-2, and feeder PBMC (e.g., irradiated allogeneic PBMC).

Another embodiment of the invention provides an isolated population of cells prepared according to any of the methods described herein with respect to other aspects of the invention. The population of cells can be a heterogeneous population comprising the host cells expressing the isolated TCR, or the antigen-binding portion thereof, in addition to at least one other cell, e.g., a host cell (e.g., a PBMC), which does not express the isolated TCR, or the antigen-binding portion thereof, or a cell other than a T cell, e.g., a B cell, a macrophage, a neutrophil, an erythrocyte, a hepatocyte, an endothelial cell, an epithelial cells, a muscle cell, a brain cell, etc. Alternatively, the population of cells can be a substantially homogeneous population, in which the population comprises mainly of (e.g., consisting essentially of) host cells expressing the isolated TCR, or the antigen-binding portion thereof. The population also can be a clonal population of cells, in which all cells of the population are clones of a single PBMC expressing the isolated TCR, or the antigen-binding portion thereof, such that all cells of the population express the isolated TCR, or the antigen-binding portion thereof. In one embodiment of the invention, the population of cells is a clonal population comprising host cells expressing the isolated TCR, or the antigen-binding portion thereof, as described herein. By introducing the nucleotide sequence encoding the isolated TCR, or the antigen binding portion thereof, into host cells, the inventive methods may, advantageously, provide a population of cells that comprises a high proportion of host cells cells that express the isolated TCR and have antigenic specificity for the mutated amino acid sequence. In an embodiment of the invention, about 1% to about 100%, for example, about 1%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 96%, about 97%, about 98%, about 99%, or about 100%, or a range defined by any two of the foregoing values, of the population of cells comprises host cells that express the isolated TCR and have antigenic specificity for the mutated amino acid sequence. Without being bound to a particular theory or mechanism, it is believed that populations of cells that comprise a high proportion of host cells that express the isolated TCR and have antigenic specificity for the mutated amino acid sequence have a lower proportion of irrelevant cells that may hinder the function of the host cells, e.g., the ability of the host cells to target the destruction of cancer cells and/or treat or prevent cancer.

The inventive TCRs, or the antigen-binding portions thereof, and populations of cells can be formulated into a composition, such as a pharmaceutical composition. In this regard, the invention provides a pharmaceutical composition comprising any of the inventive TCRs, or the antigen-binding portions thereof, or populations of cells and a pharmaceutically acceptable carrier. The inventive pharmaceutical composition can comprise an inventive TCR, or an antigen-binding portion thereof, or population of cells in combination with another pharmaceutically active agent(s) or drug(s), such as a chemotherapeutic agents, e.g., asparaginase, busulfan, carboplatin, cisplatin, daunorubicin, doxorubicin, fluorouracil, gemcitabine, hydroxyurea, methotrexate, paclitaxel, rituximab, vinblastine, vincristine, etc.

Preferably, the carrier is a pharmaceutically acceptable carrier. With respect to pharmaceutical compositions, the carrier can be any of those conventionally used for the particular inventive TCR, or the antigen-binding portion thereof, or population of cells under consideration. Such pharmaceutically acceptable carriers are well-known to those skilled in the art and are readily available to the public. It is preferred that the pharmaceutically acceptable carrier be one which has no detrimental side effects or toxicity under the conditions of use.

The choice of carrier will be determined in part by the particular inventive TCR, the antigen-binding portion thereof, or population of cells, as well as by the particular method used to administer the inventive TCR, the antigen-binding portion thereof, or population of cells. Accordingly, there are a variety of suitable formulations of the pharmaceutical composition of the invention. Suitable formulations may include any of those for oral, parenteral, subcutaneous, intravenous, intramuscular, intraarterial, intrathecal, or interperitoneal administration. More than one route can be used to administer the inventive TCR or population of cells, and in certain instances, a particular route can provide a more immediate and more effective response than another route.

Preferably, the inventive TCR, the antigen-binding portion thereof, or population of cells is administered by injection, e.g., intravenously. When the inventive population of cells is to be administered, the pharmaceutically acceptable carrier for the cells for injection may include any isotonic carrier such as, for example, normal saline (about 0.90% w/v of NaCl in water, about 300 mOsm/L NaCl in water, or about 9.0 g NaCl per liter of water), NORMOSOL R electrolyte solution (Abbott, Chicago, Ill.), PLASMA-LYTE A (Baxter, Deerfield, Ill.), about 5% dextrose in water, or Ringer's lactate. In an embodiment, the pharmaceutically acceptable carrier is supplemented with human serum albumin.

It is contemplated that the inventive TCRs, the antigen-binding portions thereof, populations of cells, and pharmaceutical compositions can be used in methods of treating or preventing cancer. Without being bound to a particular theory or mechanism, the inventive TCRs, or the antigen-binding portions thereof, are believed to bind specifically to a mutated amino acid sequence encoded by a cancer-specific mutation, such that the TCR, or the antigen-binding portion thereof, when expressed by a cell, is able to mediate an immune response against a target cell expressing the mutated amino acid sequence. In this regard, an embodiment of the invention provides a method of treating or preventing cancer in a mammal, comprising administering to the mammal any of the inventive pharmaceutical compositions, isolated pairs of TCR alpha and beta chain sequences, antigen-binding portions thereof, or populations of cells described herein, in an amount effective to treat or prevent cancer in the mammal.

Another embodiment of the invention provides any of the inventive TCRs or antigen-binding portions thereof, populations of cells, or pharmaceutical compositions described herein with respect to other aspects of the invention for use in treating or preventing cancer in a mammal.

The terms "treat," and "prevent" as well as words stemming therefrom, as used herein, do not necessarily imply 100% or complete treatment or prevention. Rather, there are varying degrees of treatment or prevention of which one of ordinary skill in the art recognizes as having a potential benefit or therapeutic effect. In this respect, the inventive methods can provide any amount of any level of treatment or prevention of cancer in a mammal. Furthermore, the treatment or prevention provided by the inventive method can include treatment or prevention of one or more conditions or symptoms of the cancer being treated or prevented. For example, treatment or prevention can include promoting the regression of a tumor. Also, for purposes herein, "prevention" can encompass delaying the onset of the cancer, or a symptom or condition thereof.

For purposes of the invention, the amount or dose of the inventive TCR, the antigen-binding portion thereof, population of cells, or pharmaceutical composition administered (e.g., numbers of cells when the inventive population of cells is administered) should be sufficient to effect, e.g., a therapeutic or prophylactic response, in the mammal over a reasonable time frame. For example, the dose of the inventive TCR, the antigen-binding portion thereof, population of cells, or pharmaceutical composition should be sufficient to bind to a mutated amino acid sequence encoded by a cancer-specific mutation, or detect, treat or prevent cancer in a period of from about 2 hours or longer, e.g., 12 to 24 or more hours, from the time of administration. In certain embodiments, the time period could be even longer. The dose will be determined by the efficacy of the particular inventive TCR, the antigen-binding portion thereof, population of cells, or pharmaceutical composition administered and the condition of the mammal (e.g., human), as well as the body weight of the mammal (e.g., human) to be treated.

Many assays for determining an administered dose are known in the art. For purposes of the invention, an assay, which comprises comparing the extent to which target cells are lysed or IFN-γ is secreted by T cells expressing the inventive TCR, or the antigen-binding portion thereof, upon administration of a given dose of such T cells to a mammal among a set of mammals of which is each given a different dose of the T cells, could be used to determine a starting dose to be administered to a mammal. The extent to which target cells are lysed or IFN-γ is secreted upon administration of a certain dose can be assayed by methods known in the art.

The dose of the inventive TCR, the antigen-binding portion thereof, population of cells, or pharmaceutical composition also will be determined by the existence, nature and extent of any adverse side effects that might accompany the administration of a particular inventive TCR, the antigen-binding portion thereof, population of cells, or pharmaceutical composition. Typically, the attending physician will decide the dosage of the inventive TCR, the antigen-binding portion thereof, population of cells, or pharmaceutical composition with which to treat each individual patient, taking into consideration a variety of factors, such as age, body weight, general health, diet, sex, inventive TCR, the antigen-binding portion thereof, population of cells, or pharmaceutical composition to be administered, route of administration, and the severity of the condition being treated.

In an embodiment in which the inventive population of cells is to be administered, the number of cells administered per infusion may vary, for example, in the range of one million to 100 billion cells; however, amounts below or above this exemplary range are within the scope of the invention. For example, the daily dose of inventive host cells can be about 1 million to about 150 billion cells (e.g., about 5 million cells, about 25 million cells, about 500 million cells, about 1 billion cells, about 5 billion cells, about 20 billion cells, about 30 billion cells, about 40 billion cells, about 60 billion cells, about 80 billion cells, about 100 billion cells, about 120 billion cells, about 130 billion cells, about 150 billion cells, or a range defined by any two of the foregoing values), preferably about 10 million to about 130 billion cells (e.g., about 20 million cells, about 30 million cells, about 40 million cells, about 60 million cells, about 70 million cells, about 80 million cells, about 90 million cells, about 10 billion cells, about 25 billion cells, about 50 billion cells, about 75 billion cells, about 90 billion cells, about 100 billion cells, about 110 billion cells, about 120 billion cells, about 130 billion cells, or a range defined by any two of the foregoing values), more preferably about 100 million cells to about 130 billion cells (e.g., about 120 million cells, about 250 million cells, about 350 million cells, about 450 million cells, about 650 million cells, about 800 million cells, about 900 million cells, about 3 billion cells, about 30 billion cells, about 45 billion cells, about 50 billion cells, about 75 billion cells, about 90 billion cells, about 100 billion cells, about 110 billion cells, about 120 billion cells, about 130 billion cells, or a range defined by any two of the foregoing values).

For purposes of the inventive methods, wherein populations of cells are administered, the cells can be cells that are allogeneic or autologous to the mammal. Preferably, the cells are autologous to the mammal.

Another embodiment of the invention provides any of the inventive TCRs, the antigen-binding portions thereof, isolated population of cells, or pharmaceutical compositions described herein for use in treating or preventing cancer in a mammal.

The cancer may, advantageously, be any cancer, including any of acute lymphocytic cancer, acute myeloid leukemia, alveolar rhabdomyosarcoma, bone cancer, brain cancer, breast cancer, cancer of the anus, anal canal, or anorectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vagina, cancer of the vulva, cholangiocarcinoma, chronic lymphocytic leukemia, chronic myeloid cancer, colon cancer, esophageal cancer, uterine cervical cancer, gastrointestinal carcinoid tumor, glioma, Hodgkin lymphoma, hypopharynx cancer, kidney cancer, larynx cancer, liver cancer, lung cancer, malignant mesothelioma, melanoma, multiple myeloma, nasopharynx cancer, non-Hodgkin lymphoma, cancer of the oropharynx, ovarian cancer, cancer of the penis, pancreatic cancer, peritoneum, omentum, and mesentery cancer, pharynx cancer, prostate cancer, rectal cancer, renal cancer, skin cancer, small intestine cancer, soft tissue cancer, stomach cancer, testicular cancer, thyroid cancer, cancer of the uterus, ureter cancer, urinary bladder cancer, solid tumors, and liquid tumors. Preferably, the cancer is an epithelial cancer. In an embodiment, the cancer is cholangiocarcinoma, melanoma, colon cancer, or rectal cancer.

The mammal referred to in the inventive methods can be any mammal. As used herein, the term "mammal" refers to any mammal, including, but not limited to, mammals of the order Rodentia, such as mice and hamsters, and mammals of the order Logomorpha, such as rabbits. It is preferred that the mammals are from the order Carnivora, including Felines (cats) and Canines (dogs). Preferably, the mammals are from the order Artiodactyla, including Bovines (cows)

and Swines (pigs) or of the order Perssodactyla, including Equines (horses). Preferably, the mammals are of the order Primates, Ceboids, or Simoids (monkeys) or of the order Anthropoids (humans and apes). A more preferred mammal is the human. In an especially preferred embodiment, the mammal is the patient expressing the cancer-specific mutation.

The following examples further illustrate the invention but, of course, should not be construed as in any way limiting its scope.

Examples 1-5

The following materials and methods were employed for the experiments described in Examples 1-5.

Screening of Neoantigen-Reactive TILs

Figure 1:
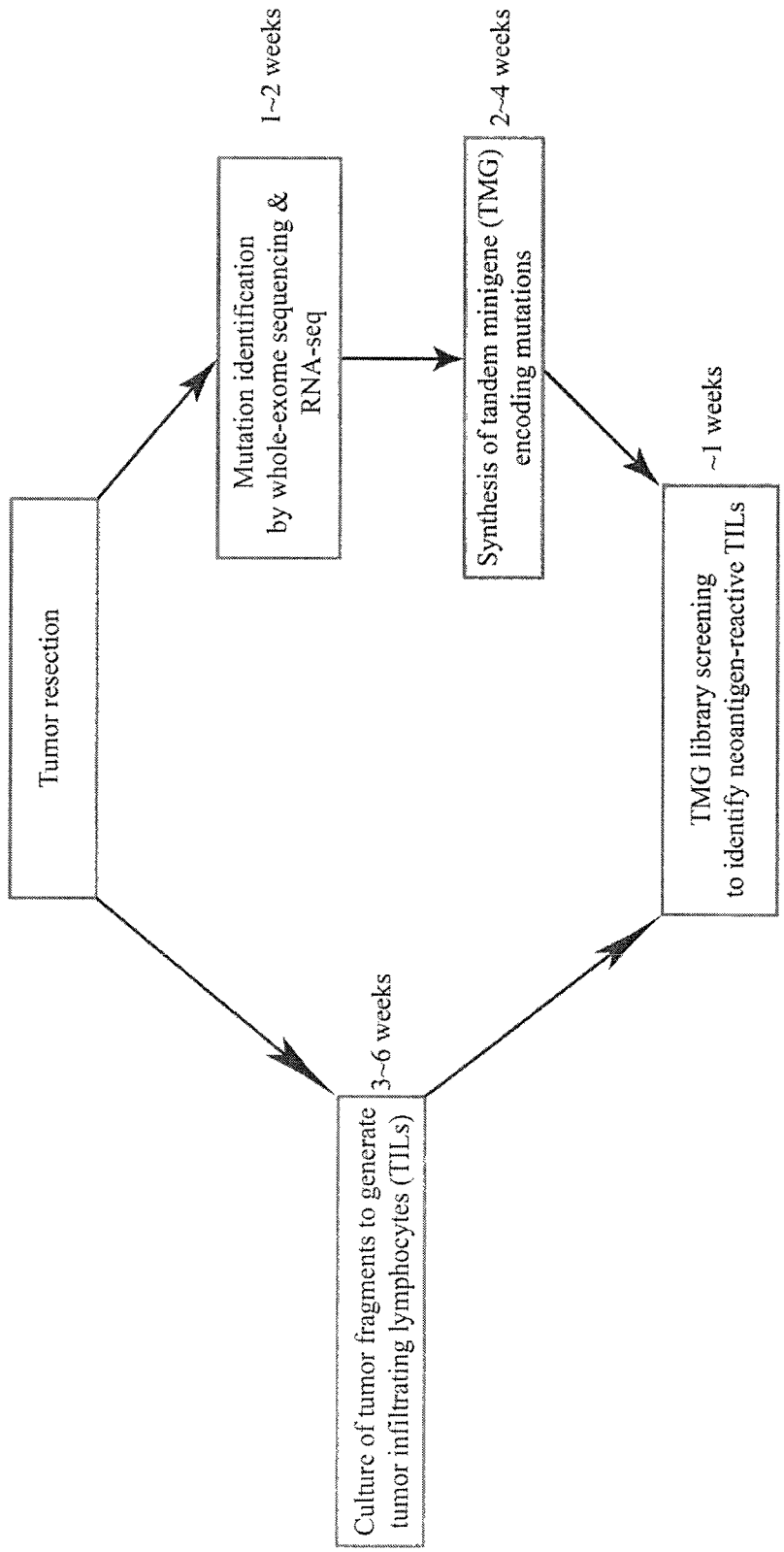
FIG. 1 is a schematic illustrating a method of identifying neoantigen-reactive TILs.

All patient materials were obtained from National Cancer Institute Institutional Review Board-approved clinical trial (Trial registration ID: NCT01174121). The method of identifying neoantigens and neoantigen-reactive TIL populations has been described in WO 2016/053338. Briefly, tumor fragments were excised and cultured in media containing IL-2 (6000 IU/mL) for 3 to 6 weeks (Dudley et al., *J. Immunother.*, 26: 332-342 (2003)). TIL cultures with expanded numbers of cells were screened for the recognition of neoantigens. To screen the expanded TIL cultures for the recognition of neoantigens, nonsynonymous mutations were identified in tumors by whole-exome and RNA sequencing (RNA-seq). Tandem minigene (TMG) libraries encompassing the nonsynonymous mutationswere synthesized. Autologous dendritic cells (DCs) expressing the TMG were screened to identify the neoantigen(s) recognized by the TILs (Lu et al., *Clin. Cancer Res.*, 20: 3401-3410 (2014)) (see FIG. 1).

Figure 2:
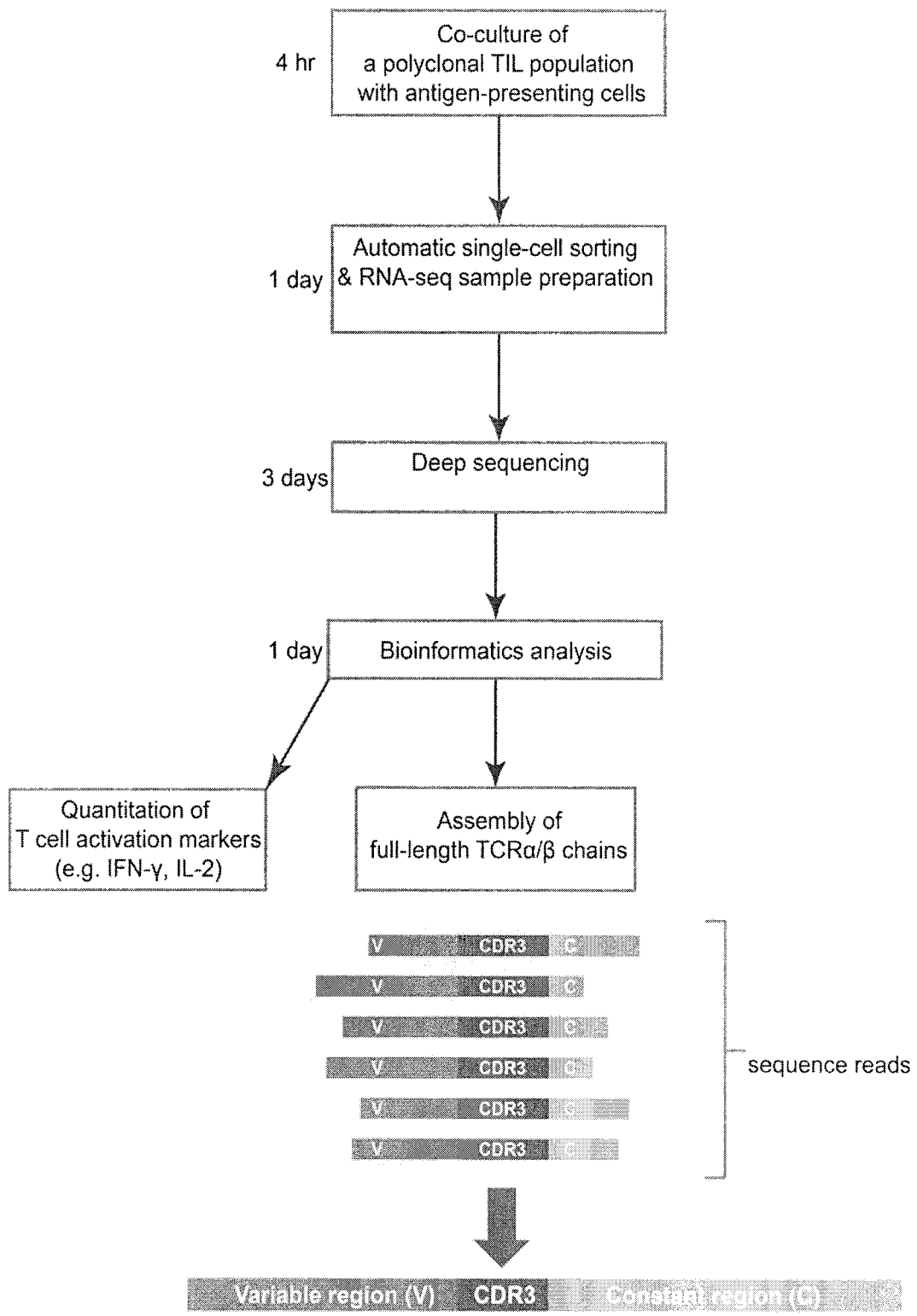
FIG. 2 is a schematic illustrating a method of identifying neoantigen-specific TCRs.

Identification of Neoantigen-Specific TCR Sequences from Single-Cell RNA-Seq Data A method of identifying neoantigen-specific TCR sequences from single-cell RNA sequencing (RNA-seq) data is summarized in the schematic shown in FIG. 2. After the neoantigen-reactive TIL cultures were identified, $1 \times 10^6$ TILs were co-cultured with $1 \times 10^6$ TMG-pulsed DCs for four (4) hours (hr). After co-culture, the T cells were re-suspended and washed extensively. Then the T cells were subjected to single-cell sorting and RNA-seq sample preparation according to the manufacturers' instructions (Fluidigm (San Francisco, Calif.) and Clontech (Mountain View, Calif.)). All 96 single-cell RNA-seq samples were barcoded using the NEXTERA XT DNA Library Preparation Kit (Illumina (San Diego, Calif.)) and were then sequenced using the ILLUMINA MISEQ system using the reagent kit V3 (2×250 base pairs (b.p.)).

Single-cell RNA-seq data were aligned by Burrows-Wheeler Aligner (BWA) (Li et al., *Bioinformatics*, 25: 1754-60 (2009); Li et al., *Bioinformatics*, 26(5): 589-95 (2010)) using TCRα/β variable (V) region sequences from the international immunogenetics information system (IMGT) database (Lefranc et al., *Nucleic Acids Res.*, 43: D413-422 (2015)). CDR3 region sequences were identified based on the conservative amino acid residues (C . . . F/W) near the C-terminus of the V region, analyzed and reported by software. Some TCRs with non-productive (out of frame) sequences were removed from the analysis. Additionally, some samples may have contained more than one T cell due to the imperfect sorting mechanism of the FLUIDIGM C1 single-cell mRNA sequencing system. As a result, samples with more than one TCRβ were eliminated from the subsequent analysis. Separately, RNA-seq data were aligned against the sequence of IFN-γ, IL-2 or other potential T cell activation markers. Aligned TCR fragments that associated with high IFN-γ single-cells were extracted, and TCR V, CDR3 and constant (C) regions were identified. To assemble paired full-length TCR sequences, incomplete 5' V region sequences were assembled with the identified human full-length TCR V region sequences from the IMGT database. To enhance pairing and avoid mispairing of TCRα/β, the 3' C region sequences were replaced with modified mouse constant region sequences (Cohen et al., *Cancer Res.*, 66: 8878-8886 (2006); Cohen et al., *Cancer Res.*, 67: 3898-3903 (2007); Haga-Friedman et al., *J. Immunol.*, 188: 5538-5546 (2012)) (FIG. 2).

Validation of Neoantigen-Specific TCRs

The detailed protocol has been described in Morgan et al., *Science*, 314: 126-129 (2006), with some minor modifications described here. Full-length TCRα and TCRβ sequences with modified mouse constant regions, linked by a furin SGSGP2A linker (RAKRSGSGATNFSLLKQAGD-VEENPGP) (SEQ ID NO: 1), were synthesized and cloned into a MSGV8 retroviral expression vector (Wargo et al., *Cancer Immunol. Immunother.*, 58: 383-394 (2009)). MSGV8-TCR plasmid (1.5 µg) and 0.75 µg of VSV-G (RD114) plasmid were co-transfected into $1 \times 10^6$ 293 GP cells in each 6-well using LIPOFECTAMINE 2000 Transfection Reagent (Thermo Fisher Scientific). After 48 hr, the supernatant was harvested and spun at 3000 revolutions per minute (rpm) for 10 minutes (min) to remove debris. The retrovirus supernatant was loaded on RETRONECTIN reagent (Takara, Otsu, Japan) coated 6-well plates by centrifugation at 2000 g for 2 hr.

Separately, $1 \times 10^6$/mL PBMCs from healthy donors were stimulated with 50 ng/mL anti-CD3 mAb OKT3 and 300 IU/mL IL-2 in AIM V medium containing 5% human serum. After 2 days, stimulated cells were harvested and re-suspended in the same medium without OKT3. Stimulated PBMCs were added to each retrovirus-loaded well at $2 \times 10^6$ cells/well and spun at 1000 g for 10 min. Plates were incubated overnight at 37° C. The next day, the PBMCs were transferred to new retrovirus-loaded wells, and the transduction procedure was repeated. TCR-transduced T cells were continuously cultured in AIM V medium with 300 IU/mL IL-2 and 5% human serum for 5 more days before experiments.

To test the specificity of TCR-transduced T cells, autologous DCs or EBV-transformed B cells were pulsed with TMG RNA, full-length mRNA or peptides for 24 hr. $1 \times 105$ T cells were then co-cultured with $1 \times 10^5$ DCs or EBV-transformed B cells overnight in 96-well U-bottom plates. The supernatant was harvested, and the secretion of IFN-γ from T cells was determined by enzyme-linked immunosorbent assay (ELISA) (Thermo Fisher Scientific).

Example 1

This example demonstrates a method of isolating the paired alpha and beta chain sequences of a neoantigen-specific TCR from the TIL 4090 culture.

TIL 4090 cultures were grown from a metastatic lung lesion resected from a patient with colorectal cancer. One of the cultures, TIL 4090 F7, recognized TMG-5 based on the results of TMG library screening. To isolate the neoantigen-specific TCR, TIL 4090 F7 cells were co-cultured with TMG-5-pulsed autologous DCs for 4 hr and subjected to single-cell RNA-seq analysis. Among all of the sequence reads in the single-cell RNA-seq data, two single cells expressed high percentages of IFN-γ reads (6.42% and 12.25% of the total R1 reads) (FIG. 3A). The rest of the single cells only expressed 0~0.16% of IFN-γ reads (FIG. 3A). None of the single cells expressed detectable IL-2 using this approach (FIG. 3B). These data suggested that these two T cells specifically reacted to neoantigens presented by DCs. Next, the TCRα/β variable regions and CDR3 sequences were identified from the single-cell RNA-seq data of these two T cells, and the TCR sequences from both T cells were identical (Table 1).

TABLE 1

| TCR variable region | CDR3 (nucleotide sequence) | CDR3 (amino acid sequence) |
|---|---|---|
| TRAV3 | TGTGCTGTGAGAGACCATAG CAACTATCAGTTAATCTGG (SEQ ID NO: 6) | CAVRDHSNYQLIW (SEQ ID NO: 7) |
| TRBV14 | TGTGCCAGCAGCCAATCCGG TGGGGGCGGGTTCTCCTACA ATGAGCAGTTCTTC (SEQ ID NO: 8) | CASSQSGGGGFSYN EQFF (SEQ ID NO: 9) |

Example 2

This example demonstrates that T cells transduced with the TCR alpha and beta chain sequences isolated in Example 1 specifically recognize a neoantigen expressed by the cancer of the patient of Example 1.

Figures 3C, 3D:
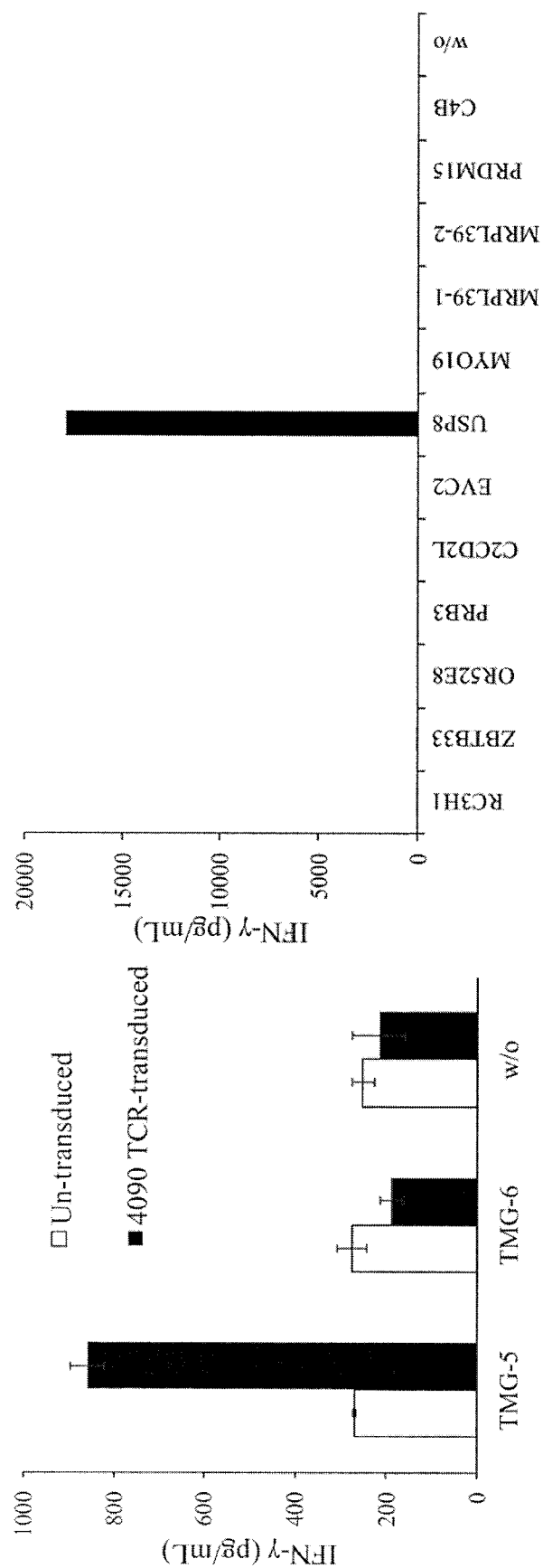
FIG. 3C is a graph showing the amount of IFN-γ (pg/mL) secreted by donor T cells which were untransduced (unshaded bars) or transduced with the 4090 TCR (shaded bars) upon co-culture with DCs pulsed with TMG-5 or TMG-6. DCs pulsed with no TMG ("w/o") served as a negative control.
FIG. 3D is a graph showing the amount of IFN-γ (pg/mL) secreted by 4090 TCR-transduced T cells upon co-culture with 4090 DCs which had been pulsed with a mutated 25-mer peptide corresponding to one of the indicated minigenes from TMG-5.

To validate the TCR isolated from TIL 4090 F7, the full-length TCRα and TCRβ sequences with modified mouse constant regions, linked by a furin SGSGP2A linker, were synthesized and cloned into a MSGV8 retroviral expression vector. Peripheral blood T cells were transduced with the 4090 TCR and co-cultured with TMG-5-pulsed 4090 DCs overnight. Based on the secretion of IFN-γ by T cells, 4090 TCR-transduced T cells recognized TMG-5-pulsed DCs, but not DCs pulsed with irrelevant TMG (FIG. 3C).

Figure 3E:
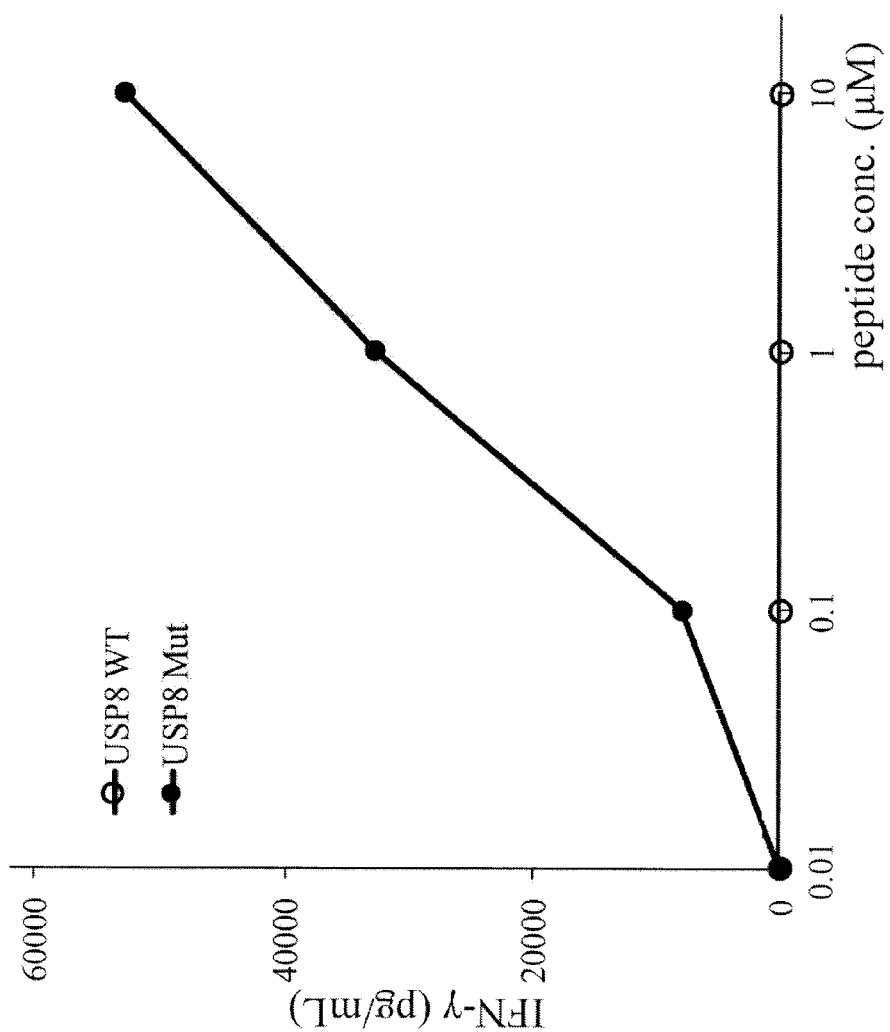
FIG. 3E is a graph showing the amount of IFN-γ (pg/mL) secreted by 4090 TCR-transduced T cells upon co-culture with 4090 DCs which had been pulsed with the indicated concentration (conc.) (μM) of purified 25-mer WT (open circles) or mutated (closed circles) USP8 peptide.

Additional experiments were carried out to test the specificity of the 4090 TCR. TMG-5 contained a total of 12 minigenes. 25-mer mutated long-peptides corresponding to each minigene were synthesized and pulsed onto 4090 DCs for 24 hr. After washing, peptide-pulsed DCs were co-cultured with the 4090 TCR-transduced T cells overnight. The 4090 TCR-transduced T cells only reacted to the DCs pulsed with mutated USP8 (ubiquitin specific peptidase 8) peptide WAKFLDPITGTFHYYHSPTNTVHMY (R>H) (SEQ ID NO: 2), suggesting that the 4090 TCR recognized mutated USP8 (FIG. 3D). Lastly, high performance liquid chromatography (HPLC)-purified mutated USP8 long-peptide and the wild type (WT) counterpart were pulsed on 4090 DCs for 24 hr. Then, peptide-pulsed DCs were co-cultured with 4090 TCR-transduced T cells overnight. The 4090 TCR-transduced T cells reacted to the mutated USP8 peptide at a minimum concentration of 0.01 µM, but showed no significant recognition of WT USP8 peptide. (FIG. 3E).

Example 3

This example demonstrates a method of isolating the paired alpha and beta chain sequences of a neoantigen-specific TCR from the TIL 4095 culture.

Figure 4C:
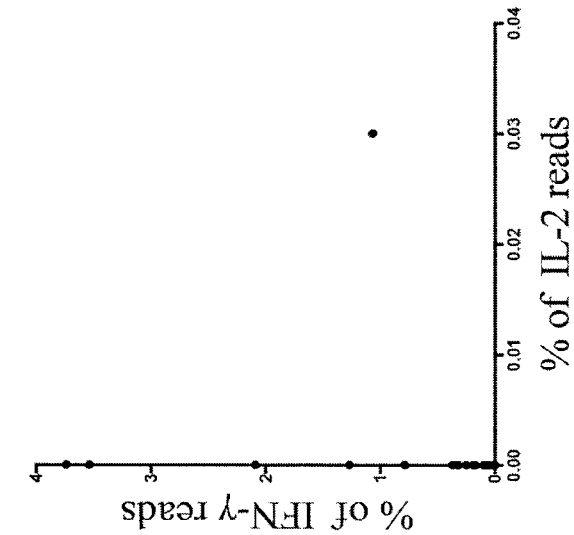
FIG. 4C is a graph showing the percentage of IFN-γ and IL-2 reads within the total R1 reads measured in the single cell which expressed detectable IL-2 reads in FIG. 4B.
Figure 4B:
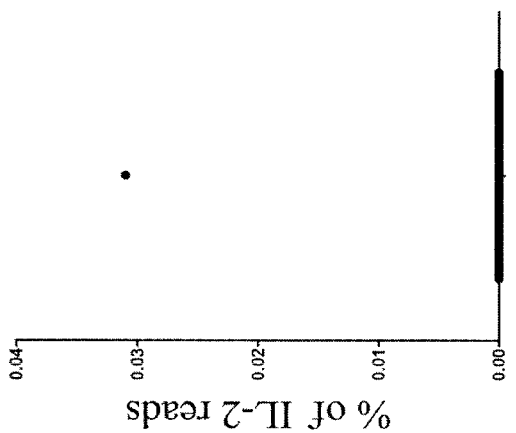
FIG. 4A and FIG. 4B are graphs showing the percentage of IFN-γ (A) and IL-2 (B) reads within the total R1 reads measured in 4095 F5 T cells that were co-cultured with TMG-1-pulsed autologous DCs for 4 hr and then subjected to single-cell RNA-seq analysis.
Figure 4A:
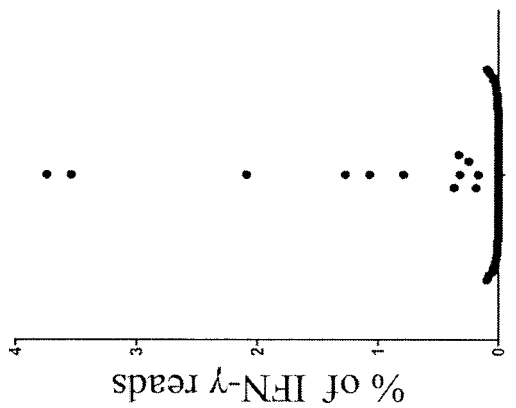

TIL 4095 cultures were grown from metastatic lung lesions resected from a patient with colorectal cancer. TIL 4095 F5 recognized TMG-1 based on the results of TMG library screening. To isolate the neoantigen-specific TCR, TIL 4095 F5 cells were co-cultured with TMG-1-pulsed autologous DCs for 4 hr and subjected to single-cell RNA-seq analysis. All single-cells with high levels of IFN-γ reads (0.79%~3.74%) were identified (FIG. 4A). These T cells all contained exactly the same TCRα/β variable and CDR3 sequences (Table 2). Only one single-cell expressed detectable IL-2 reads (0.03%) (FIG. 4B), and this single cell co-expressed IFN-γ at a high level (1.07%) (FIG. 4C).

TABLE 2

| TCR variable region | CDR3 (nucleotide sequence) | CDR3 (amino acid sequence) |
|---|---|---|
| TRAV4 | TGCCTCGTGGGTGACATGGA CCAGGCAGGAACTGCTCTGA TCTTT (SEQ ID NO: 10) | CLVGDMDQAGTALIF (SEQ ID NO: 11) |
| TRBV5-6 | TGTGCCAGCAGCTTGGGGAG GGCAAGCAATCAGCCCCAGC ATTTT (SEQ ID NO: 12) | CASSLGRASNQPQHF (SEQ ID NO: 13) |

Example 4

This example demonstrates that T cells transduced with the TCR alpha and beta chain sequences isolated in Example 3 specifically recognize a neoantigen expressed by the cancer of the patient of Example 3.

Figure 4E:
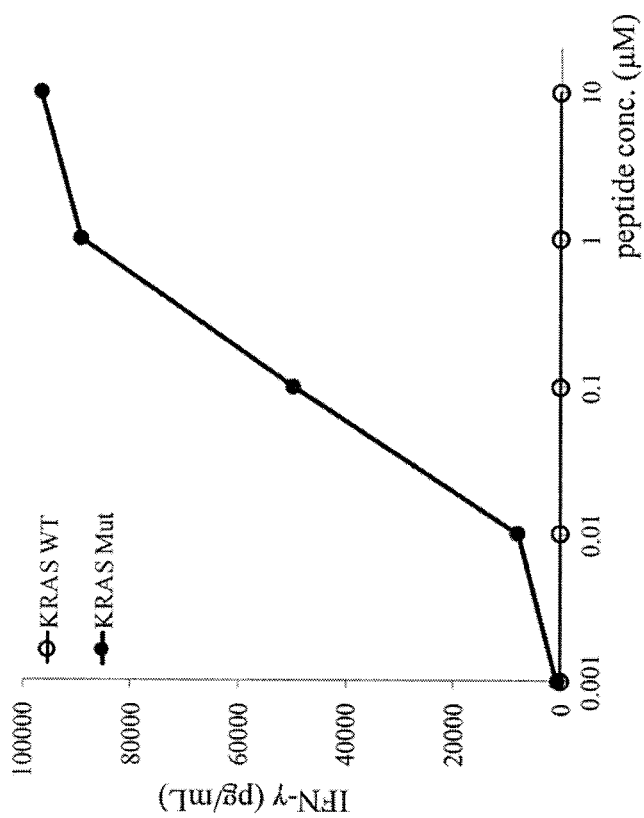
FIG. 4E is a graph showing the amount of IFN-γ (pg/mL) secreted by 4095 TCR-transduced T cells upon co-culture with 4095 DCs which had been pulsed with the indicated concentrations (μM) of a purified 9-mer WT (open circles) or mutated (closed circles) KRAS peptide.
Figure 4D:
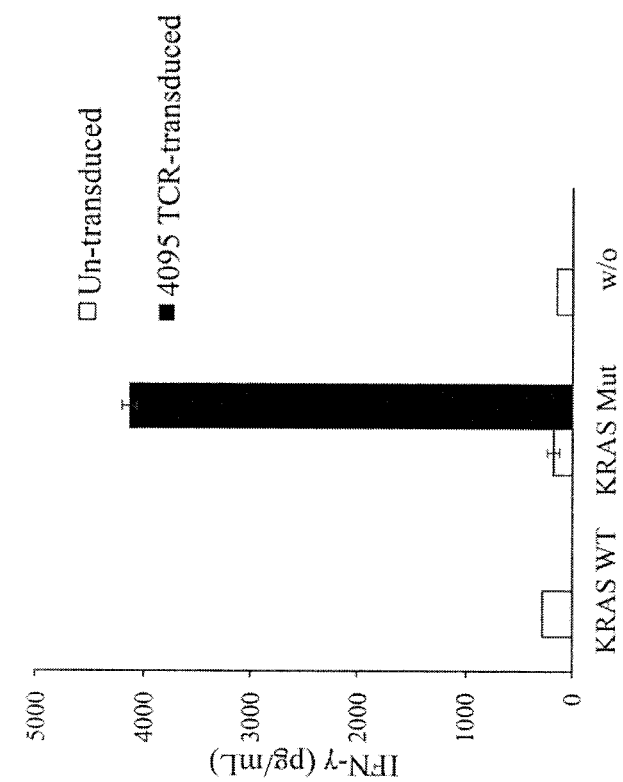
FIG. 4D is a graph showing the amount of IFN-γ (pg/mL) secreted by donor T cells which were untransduced (unshaded bars) or transduced with the 4095 TCR (shaded bars) upon co-culture with DCs pulsed with full-length WT or mutated KRAS mRNA. DCs pulsed with no peptide ("w/o") served as a negative control.

To validate the TCR isolated from TIL 4095 F5 of Example 3, the full-length TCRα and TCRβ sequences with modified mouse constant regions were synthesized and cloned into a MSGV8 retroviral expression vector, and then transduced into donor T cells. In a previous study, a TCR which recognizes a mutated KRAS(G12D) peptide in an HLA-00802-restricted manner was identified (Tran et al., Science, 350: 1387-1390 (2015)). Because patient 4095 was found to be positive for HLA-00802 and KRAS(G12D), and because TMG-1 encoded KRAS(G12D), whether this 4095 TCR also recognized HLA-C0802-restricted KRAS (G12D) was tested. As shown in FIG. 4D, 4095 TCR-transduced T cells were co-cultured with full-length KRAS WT or G12D mRNA-pulsed autologous DCs overnight. 4095 TCR-transduced T cells recognized KRAS(G12D)-pulsed DCs, but not DCs pulsed with WT KRAS. Lastly, autologous DCs were pulsed with the minimum epitope GADGVGKSA (SEQ ID NO: 3) of HLA-00802-restricted KRAS(G12D) antigen for 2 hours. 4095 TCR-transduced T cells recognized the KRAS (G12D) epitope at a minimum concentration of 0.01 µM and did not recognize the WT counterpart (FIG. 4E).

Example 5

This example demonstrates a method of isolating the paired alpha and beta chain sequences of a neoantigen-specific TCR from the TIL 4112 culture.

TIL 4112 cultures were grown from a metastatic liver lesion resected from a patient with cholangiocarcinoma. One of the cultures, TIL 4112 F5, was found to recognize TMG-9 based on the results of TMG library screening. To identify the neoantigen-specific TCR, TIL 4112 F5 cells were co-cultured with TMG-9-pulsed autologous DCs for 4 hr and subjected to single-cell RNA-seq analysis. Twenty-two (22) single-cells with high levels of IFN-γ reads (>2%) contained exactly the same TCR sequences (FIG. 5A, FIG. 5C, and Table 3). However, 13 out of 22 single-cells did not contain detectable TCRα due to the low level of TCRα expression in this clonotype. Eight (8) single-cells expressed detectable IL-2 reads, ranging from 0.01%~0.1% (FIG. 5B and FIG. 5C). Among them, 6 single-cells expressed the same TCRα/β sequences. One single-cell expressed the identical TCRβ sequence, but the TCRα was not detectable. In addition, one single cell did not express any detectable TCRα/β sequences (FIGS. 5A-5C).

TABLE 3

| TCR variable region | CDR3 (nucleotide sequence) | CDR3 (amino acid sequence) |
|---|---|---|
| TRAV38-1 | TGTGCTTTCATGTGGGGATT AGGTCAGAATTTTGTCTTT (SEQ ID NO: 14) | CAFMWGLGQNFVF (SEQ ID NO: 15) |
| TRBV28 | TGTGCCAGCAGTGTGGAGCG GGAGAACACCGGGGAGCTGT TTTTT (SEQ ID NO: 16) | CASSVERENTGELFF (SEQ ID NO: 17) |

To validate the TCR identified from TIL 4112 F5, the full-length TCRα and TCRβ sequences with modified mouse constant regions were synthesized and then transduced into donor T cells. The 4112 TCR-transduced T cells recognized TMG-9-pulsed DCs, but not DCs pulsed with irrelevant TMG (FIG. 5D). Next, the amino acid sequence of TMG-9 was submitted to the Immune Epitope Database (IEDB) And Analysis Resource website (iedb.org) and Center for Biological Sequence (CBS) Analysis NetMHC website (cbs.dtu.dk/services/NetMHC/) to predict peptides with high affinity to the 6 HLAs of patient 4112. A total of 67 predicted high-affinity peptides from IEDB (Rank<1%) and NetMHC (Rank<2%) were synthesized and combined into 10 pools. The 4112 TCR-transduced T cells recognized the short peptide pool (SPP)-9 pulsed on autologous EBV-transfoinied B cells (FIG. 5E). In subsequent experiments, the mutated NBAS (neuroblastoma amplified sequence) peptide WSYDSTLLAY (C>S) (SEQ ID NO: 4) was identified as the minimum epitope recognized by 4112 TCR-transduced T cells (FIG. 5F, 5G).

Example 6

This example demonstrates a method of isolating the paired alpha and beta chain sequences of a neoantigen-specific TCR from the TIL 4171 culture.

TIL 4171 cultures were grown from a metastatic lung lesion resected from a patient with colorectal cancer. 128 long-peptides (25-mer) were synthesized, and each peptide contained a nonsynonymous mutation flanked on both sides by 12 normal amino acids. TIL 4171 cultures were screened against the peptide library, and one of the cultures, TIL4171F6, recognized peptide pool 3 (PP-3) (FIG. 9A). TIL4171F6 cells were then co-cultured with PP-3-pulsed autologous DCs for 4 hr, and subjected to single-cell RNA-seq analysis. Expression of IFN-γ and IL-2 was measured (FIGS. 9B-9D). Nine samples contained high levels of IFN-γ mRNA (2209~24845 FPKM (Fragments Per Kilobase of transcript per Million mapped reads)) (FIG. 9B). Among them, six samples had the same TCRβ CDR3 sequence. Two samples did not contain any detectable TCRβ, and one sample contained two different TCR CDR3 sequences, which likely resulted from contamination by another T cell. However, none of these samples contained any detectable TCRα chain sequences. Similarly, four samples contained detectable IL-2 mRNA (331.2~1497 FPKM). These samples all contained the identical TCRβ CDR3 sequence, but none of the samples had any detectable TCRα chain sequence.

In an attempt to discover the missing TCRα chain, the single-cell RNA-seq data obtained in this experiment was further investigated. It was found that four IFN-γ⁺ single cells and two IL-2⁺ single cells expressed a unique TCR chain, which included a V gene segment DV3, a J gene segment AJ56 and a C gene segment AC. Several V gene segments are shared between TCRα and TCRδ chains, including AV14/DV4, AV23/DV6, AV29/DV5, AV36/DV7, and AV38-2/DV8 (Lefranc, Current Protocols in Immunology, John Wiley & Sons, Inc., pp. A.1O.1-A.1O.23 (2001)). These V gene segments have been found to be rearranged to AJ joining gene segments for TCRα, and to be rearranged to DD diversity gene segments and DJ joining gene segments for TCRδ. Notably, the orientation of DV3 transcription is inverted. So far, it has not been reported that a TCRα chain can utilize a DV3 gene segment.

To test the function of this unique TCR chain, this TCR chain was linked to the identified TCRβ chain and then cloned into a retroviral vector. 4171TCR-transduced T cells were strongly reactive to PP-3 (FIG. 9E). This peptide pool PP-3 contained 14 mutated 25-mer-peptides.

Next, autologous DCs were pulsed with individual peptides from peptide pool PP-3 for 24 hours. Peptide-pulsed DCs were co-cultured with 4171TCR-transduced T cells. 4171TCR recognized mutated peptide SIN3A (SIN3 transcription regulator family member A)-pulsed DCs (FIG. 9F).

Lastly, purified 25-mer WT or mutated SIN3A peptide (LGKFPELFNWFKIFLGYKESVHLET (SEQ ID NO: 25), N>I), was pulsed on autologous DCs for 24 hr. Peptide-pulsed DCs were co-cultured with transduced T cells. The secretion of IFN-γ from T cells was determined by ELISA. 4171TCR-transduced T cells were shown to specifically recognize mutated SIN3A peptide, but not the wild-type counterpart (FIG. 9G).

Therefore, this unique TCR was functional, and it could specifically recognize mutated SIN3A. Similar to other V gene segments, these data suggested that DV3 gene segment could be shared between TCRα and TCRδ chains.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The teens "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of isolating nucleic acid(s) comprising one or more nucleotide sequences encoding a T cell receptor (TCR) comprising a TCR alpha chain polypeptide and a TCR beta chain polypeptide, or an antigen-binding portion thereof, the method comprising:
  (a) isolating, from a biological sample, T cells having antigenic specificity for a mutated amino acid sequence encoded by a cancer-specific mutation;
  (b) co-culturing the isolated T cells with antigen presenting cells (APCs) that present the mutated amino acid sequence so that the T cells express one or more T cell activation markers;
  (c) sorting the co-cultured T cells into separate single T cell samples;
  (d) isolating mRNA from each separate single T cell sample;
  (e) sequencing the mRNA from each separate single T cell sample, wherein the sequencing comprises:
    (i) producing cDNA from the mRNA and amplifying the cDNA;
    (ii) producing multiple fragments of the amplified cDNA and tagging the multiple fragments;
    (iii) amplifying the tagged, multiple fragments of the cDNA; and
    (iv) sequencing the amplified, tagged multiple fragments of the cDNA;
  wherein the sequencing identifies the sequences of each of the multiple fragments of cDNA;
  (f) aligning the sequences of each of the multiple fragments of cDNA to a known sequence of the one or more T cell activation markers to identify which single T cell sample contained a single T cell which expressed the one or more T cell activation markers;
  (g) aligning the sequences of each of the multiple fragments of cDNA to a reference TCR sequence database to identify TCR alpha chain variable (V) segment sequences and TCR beta chain V segment sequences of the multiple fragments of cDNA of each separate single T cell sample which was identified in (f) to express one or more T cell activation markers;
  (h) identifying TCR complementarity determining region 3 (CDR3) sequences in the multiple fragments of cDNA containing the TCR alpha chain V segment sequences identified in (g) and in the multiple fragments of cDNA containing the TCR beta chain V segment sequences identified in (g);
  (i) counting the number of multiple fragments of cDNA which share the same alpha chain CDR3 amino acid sequence and the number of multiple fragments of cDNA which share the same beta chain CDR3 amino acid sequence;
  (j) collecting the highest number of multiple fragments of cDNA which encode the same alpha chain CDR3 sequence, the highest number of multiple fragments of cDNA which encode the same beta chain CDR3 sequence and, optionally, the second highest number of multiple fragments of cDNA which encode the same alpha chain CDR3 sequence, wherein the alpha chain CDR3 sequence encoded by the second highest number of multiple fragments of cDNA is different from the alpha chain CDR3 sequence encoded by the highest number of multiple fragments of cDNA
  to identify the TCR alpha and beta chain CDR3 sequences;
  (k) identifying the TCR alpha chain V segment sequence of the highest number of multiple fragments of cDNA collected in (j), the TCR beta chain V segment sequence of the highest number of multiple fragments of cDNA collected in (j) and, optionally, the TCR alpha chain V segment sequence of the second highest number of multiple fragments of cDNA collected in (j)
  to identify the TCR alpha and beta chain V segment sequences; and
  (l) assembling one or more nucleic acid(s) comprising nucleotide sequences encoding:
    a TCR alpha chain polypeptide comprising the TCR alpha chain V segment sequence identified in (k) and the TCR alpha chain CDR3 sequence collected in (j) and
    a TCR beta chain polypeptide comprising the TCR beta chain V segment sequence identified in (k) and the TCR beta chain CDR3 sequence collected in (j),
  optionally assembling a second one or more nucleic acid(s) comprising nucleotide sequences encoding:
    a second TCR alpha chain polypeptide comprising the TCR alpha chain V segment sequence of the second highest number of multiple fragments of cDNA identified in (k) and the TCR alpha chain CDR3 sequence of the second highest number of multiple fragments of cDNA collected in (j) and
    the TCR beta chain polypeptide comprising the TCR beta chain V segment sequence identified in (k) and the TCR beta chain CDR3 sequence collected in (j)
  to produce isolated nucleic acid(s) comprising one or more nucleotide sequences encoding the TCR comprising the TCR alpha chain polypeptide and the TCR beta chain polypeptide, or an antigen-binding portion thereof, wherein the TCR has antigenic specificity for the mutated amino acid sequence encoded by the cancer-specific mutation.

2. The method according to claim 1, wherein the one or more T cell activation markers comprise one or more of interferon (IFN)-γ, interleukin (IL)-2, tumor necrosis factor alpha (TNF-α), programmed cell death 1 (PD-1), lymphocyte-activation gene 3 (LAG-3), T cell immunoglobulin and mucin domain 3 (TIM-3), 4-1BB, OX40, CD107a, granzyme B, granulocyte/monocyte colony stimulating factor (GM-CSF), IL-4, IL-5, IL-9, IL-10, IL-17, and IL-22.

3. The method according to claim 1, further comprising labeling the mRNA from each separate single T cell sample with a different tag for each separate single T cell sample.

4. The method according to claim 1, wherein (h) comprises identifying TCR CDR3 sequences by identifying cDNA sequences which encode conserved amino acid residues positioned near the C-terminus of the amino acid sequence which is encoded by the V segment of the alpha and beta chains.

5. The method according to claim 1, wherein (k) further comprises identifying the TCR alpha chain constant (C) region sequence of the highest number of multiple fragments of cDNA collected in (j) and the TCR beta chain C region sequence of the highest number of multiple fragments of cDNA collected in (j).

6. The method according to claim 5, wherein (l) comprises assembling nucleic acid(s) comprising one or more nucleotide sequences encoding a TCR alpha chain polypeptide comprising the TCR alpha chain V segment sequence identified in (k), the TCR alpha chain C region sequence identified in (k), and the TCR alpha chain CDR3 sequence collected in (j) and a TCR beta chain polypeptide comprising the TCR beta chain V segment sequence identified in (k), the TCR beta chain C region sequence identified in (k), and the TCR beta chain CDR3 sequence collected in (j).

7. The method according to claim 1, wherein (l) comprises assembling nucleic acid(s) comprising one or more nucleotide sequences encoding a TCR alpha chain polypeptide comprising the TCR alpha chain V segment sequence identified in (k), an exogenous TCR alpha chain C region sequence, and the TCR alpha chain CDR3 sequence collected in (j) and a TCR beta chain polypeptide comprising the TCR beta chain V segment sequence identified in (k), an exogenous TCR beta chain C region sequence, and the TCR beta chain CDR3 sequence collected in (j).

8. The method according to claim 1, further comprising receiving, at a user computing device, the sequences of the multiple fragments of cDNA of the single T cell identified in (f);
wherein (g) comprises performing computerized alignment of the sequences of each of the multiple fragments of cDNA to a reference TCR sequence database to identify TCR alpha chain variable (V) segment sequences and TCR beta chain V segment sequences of the multiple fragments of cDNA of the single T cell identified in (f);
wherein (h) comprises performing computerized identification of TCR CDR3 sequences in the multiple fragments of cDNA containing the TCR alpha chain V segment sequences identified in (g) and in the multiple fragments of cDNA containing the TCR beta chain V segment sequences identified in (g);
wherein (i) comprises performing computerized counting of the number of multiple fragments of cDNA which share the same alpha chain CDR3 amino acid sequence and the number of multiple fragments of cDNA which share the same beta chain CDR3 amino acid sequence;
wherein (j) comprises performing computerized collecting of the highest number of multiple fragments of cDNA which encode the same alpha chain CDR3 sequence, the highest number of multiple fragments of cDNA which encode the same beta chain CDR3 sequence and, optionally, the second highest number of multiple fragments of cDNA which encode the same alpha chain CDR3 sequence, wherein the alpha chain CDR3 sequence encoded by the second highest number of multiple fragments of cDNA is different from the alpha chain CDR3 sequence encoded by the highest number of multiple fragments of cDNA
to identify the TCR alpha and beta chain CDR3 sequences; and
wherein (k) comprises performing computerized identification of the TCR alpha chain V segment sequence of the highest number of multiple fragments of cDNA collected in (j), the TCR beta chain V segment sequence of the highest number of multiple fragments of cDNA collected in (j) and, optionally, the TCR alpha chain V segment sequence of the second highest number of multiple fragments of cDNA collected in (j)
to identify the TCR alpha and beta chain V segment sequences.

9. A method of preparing a population of cells that express a TCR, or an antigen-binding portion thereof, the method comprising:
isolating nucleic acid(s) comprising one or more nucleotide sequences encoding a TCR comprising a TCR alpha chain polypeptide and a TCR beta chain polypeptide, or an antigen-binding portion thereof, according to the method of claim 1, and
introducing the nucleic acid(s) into host cells to obtain cells that express the TCR, or the antigen-binding portion thereof.

10. The method of claim 9, further comprising expanding the numbers of host cells that express the TCR, or the antigen-binding portion thereof.

* * * * *

```
                         SEQUENCE LISTING

<160> NUMBER OF SEQ ID NOS: 25

<210> SEQ ID NO 1
    <211> LENGTH: 27
    <212> TYPE: PRT
    <213> ORGANISM: Homo sapiens

<400> SEQUENCE: 1

Arg Ala Lys Arg Ser Gly Ser Gly Ala Thr Asn Phe Ser Leu Leu Lys
    1               5                   10                  15

Gln Ala Gly Asp Val Glu Glu Asn Pro Gly Pro
                20                  25

<210> SEQ ID NO 2
    <211> LENGTH: 25
    <212> TYPE: PRT
    <213> ORGANISM: Homo sapiens

<400> SEQUENCE: 2

Trp Ala Lys Phe Leu Asp Pro Ile Thr Gly Thr Phe His Tyr Tyr His
    1               5                   10                  15

Ser Pro Thr Asn Thr Val His Met Tyr
                20                  25

<210> SEQ ID NO 3
    <211> LENGTH: 9
    <212> TYPE: PRT
    <213> ORGANISM: Homo sapiens

<400> SEQUENCE: 3

Gly Ala Asp Gly Val Gly Lys Ser Ala
    1               5

<210> SEQ ID NO 4
    <211> LENGTH: 10
    <212> TYPE: PRT
    <213> ORGANISM: Homo sapiens

<400> SEQUENCE: 4

Trp Ser Tyr Asp Ser Thr Leu Leu Ala Tyr
    1               5                   10

<210> SEQ ID NO 5
    <211> LENGTH: 24
    <212> TYPE: PRT
    <213> ORGANISM: Homo sapiens
    <220> FEATURE:
    <221> NAME/KEY: MISC_FEATURE
    <222> LOCATION: (2)..(2)
    <223> OTHER INFORMATION: Xaa at position 2 is any naturally occurring
          amino acid
    <220> FEATURE:
    <221> NAME/KEY: MISC_FEATURE
    <222> LOCATION: (4)..(11)
```

```
<223> OTHER INFORMATION: Xaa at each of positions 4-11 is any naturally
      occurring amino acid
<220> FEATURE:
<221> NAME/KEY: MISC_FEATURE
<222> LOCATION: (12)..(23)
<223> OTHER INFORMATION: Xaa at each of positions 12-23 is no amino acid
      or is any naturally occurring amino acid
<220> FEATURE:
<221> NAME/KEY: MISC_FEATURE
<222> LOCATION: (24)..(24)
<223> OTHER INFORMATION: Xaa at position 24 is phenylalanine or
      tryptophan

<400> SEQUENCE: 5

Tyr Xaa Cys Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa
            20

<210> SEQ ID NO 6
<211> LENGTH: 39
<212> TYPE: DNA
<213> ORGANISM: Homo sapiens

<400> SEQUENCE: 6
tgtgctgtga gagaccatag caactatcag ttaatctgg                              39

<210> SEQ ID NO 7
<211> LENGTH: 13
<212> TYPE: PRT
<213> ORGANISM: Homo sapiens

<400> SEQUENCE: 7

Cys Ala Val Arg Asp His Ser Asn Tyr Gln Leu Ile Trp
1               5                   10

<210> SEQ ID NO 8
<211> LENGTH: 54
<212> TYPE: DNA
<213> ORGANISM: Homo sapiens

<400> SEQUENCE: 8
tgtgccagca gccaatccgg tgggggcggg ttctcctaca atgagcagtt cttc            54

<210> SEQ ID NO 9
<211> LENGTH: 18
<212> TYPE: PRT
<213> ORGANISM: Homo sapiens

<400> SEQUENCE: 9

Cys Ala Ser Ser Gln Ser Gly Gly Gly Gly Phe Ser Tyr Asn Glu Gln
1               5                   10                  15

Phe Phe

<210> SEQ ID NO 10
<211> LENGTH: 45
<212> TYPE: DNA
<213> ORGANISM: Homo sapiens

<400> SEQUENCE: 10
tgcctcgtgg gtgacatgga ccaggcagga actgctctga tcttt                      45

<210> SEQ ID NO 11
<211> LENGTH: 15
<212> TYPE: PRT
```

<213> ORGANISM: Homo sapiens

<400> SEQUENCE: 11

Cys Leu Val Gly Asp Met Asp Gln Ala Gly Thr Ala Leu Ile Phe
1               5                   10                  15

<210> SEQ ID NO 12
<211> LENGTH: 45
<212> TYPE: DNA
<213> ORGANISM: Homo sapiens

<400> SEQUENCE: 12
tgtgccagca gcttggggag ggcaagcaat cagccccagc atttt          45

<210> SEQ ID NO 13
<211> LENGTH: 15
<212> TYPE: PRT
<213> ORGANISM: Homo sapiens

<400> SEQUENCE: 13

Cys Ala Ser Ser Leu Gly Arg Ala Ser Asn Gln Pro Gln His Phe
1               5                   10                  15

<210> SEQ ID NO 14
<211> LENGTH: 39
<212> TYPE: DNA
<213> ORGANISM: Homo sapiens

<400> SEQUENCE: 14
tgtgctttca tgtggggatt aggtcagaat tttgtcttt          39

<210> SEQ ID NO 15
<211> LENGTH: 13
<212> TYPE: PRT
<213> ORGANISM: Homo sapiens

<400> SEQUENCE: 15

Cys Ala Phe Met Trp Gly Leu Gly Gln Asn Phe Val Phe
1               5                   10

<210> SEQ ID NO 16
<211> LENGTH: 45
<212> TYPE: DNA
<213> ORGANISM: Homo sapiens

<400> SEQUENCE: 16
tgtgccagca gtgtggagcg ggagaacacc ggggagctgt ttttt          45

<210> SEQ ID NO 17
<211> LENGTH: 15
<212> TYPE: PRT
<213> ORGANISM: Homo sapiens

<400> SEQUENCE: 17

Cys Ala Ser Ser Val Glu Arg Glu Asn Thr Gly Glu Leu Phe Phe
1               5                   10                  15

<210> SEQ ID NO 18
<211> LENGTH: 14
<212> TYPE: PRT
<213> ORGANISM: Homo sapiens

<400> SEQUENCE: 18

Val Trp Asp Ala Leu Phe Ala Asp Gly Leu Ser Leu Cys Leu

```
1               5                   10

<210> SEQ ID NO 19
<211> LENGTH: 13
<212> TYPE: PRT
<213> ORGANISM: Homo sapiens

<400> SEQUENCE: 19

Trp Arg Arg Val Ala Trp Ser Tyr Asp Ser Thr Leu Leu
1               5                   10

<210> SEQ ID NO 20
<211> LENGTH: 8
<212> TYPE: PRT
<213> ORGANISM: Homo sapiens

<400> SEQUENCE: 20

Trp Ser Tyr Asp Ser Thr Leu Leu
1               5

<210> SEQ ID NO 21
<211> LENGTH: 9
<212> TYPE: PRT
<213> ORGANISM: Homo sapiens

<400> SEQUENCE: 21

Trp Ser Tyr Asp Ser Thr Leu Leu Ala
1               5

<210> SEQ ID NO 22
<211> LENGTH: 10
<212> TYPE: PRT
<213> ORGANISM: Homo sapiens

<400> SEQUENCE: 22

Trp Ser Tyr Asp Ser Thr Leu Leu Ala Tyr
1               5                   10

<210> SEQ ID NO 23
<211> LENGTH: 12
<212> TYPE: PRT
<213> ORGANISM: Homo sapiens

<400> SEQUENCE: 23

Tyr Leu Ala Leu Val Asp Lys Asn Ile Ile Gly Tyr
1               5                   10

<210> SEQ ID NO 24
<211> LENGTH: 9
<212> TYPE: PRT
<213> ORGANISM: Homo sapiens

<400> SEQUENCE: 24

Tyr Ser Glu Pro Asp Val Ser Gly Lys
1               5

<210> SEQ ID NO 25
<211> LENGTH: 25
<212> TYPE: PRT
```

```
<213> ORGANISM: Homo sapiens

<400> SEQUENCE: 25

Leu Gly Lys Phe Pro Glu Leu Phe Asn Trp Phe Lys Ile Phe Leu Gly
1               5                   10                  15

Tyr Lys Glu Ser Val His Leu Glu Thr
            20                  25
```